US008916616B2

(12) United States Patent
Lowe et al.

(10) Patent No.: US 8,916,616 B2
(45) Date of Patent: Dec. 23, 2014

(54) MULTI-FUNCTIONAL POLYMERIC MATERIALS AND THEIR USES

(71) Applicants: Tao Lu Lowe, Hummelstown, PA (US); Young Shin Kim, Florence, KY (US); Xiao Huang, Freehold, NJ (US)

(72) Inventors: Tao Lu Lowe, Hummelstown, PA (US); Young Shin Kim, Florence, KY (US); Xiao Huang, Freehold, NJ (US)

(73) Assignee: University of Tennessee Research Foundation, Memphis, TN (US)

( * ) Notice: Subject to any disclaimer, the term of this patent is extended or adjusted under 35 U.S.C. 154(b) by 0 days.

(21) Appl. No.: 14/011,118

(22) Filed: Aug. 27, 2013

(65) Prior Publication Data

US 2013/0344027 A1 Dec. 26, 2013

Related U.S. Application Data

(62) Division of application No. 10/807,510, filed on Mar. 24, 2004, now Pat. No. 8,545,830.

(60) Provisional application No. 60/457,499, filed on Mar. 24, 2003, provisional application No. 60/466,966, filed on May 1, 2003, provisional application No. 60/519,796, filed on Nov. 14, 2003.

(51) Int. Cl.
*A61K 47/30* (2006.01)
(Continued)

(52) U.S. Cl.
CPC ............. *A61K 47/34* (2013.01); *C08B 37/0021* (2013.01); *A61K 9/0024* (2013.01); *C08G 83/003* (2013.01); *A61K 9/0019* (2013.01); *A61K 9/06* (2013.01); *B82Y 30/00* (2013.01); *C08L 101/16* (2013.01)

USPC .................... 514/772.1; 424/85.2; 424/130.1; 424/184.1; 424/85.4; 424/94.1; 424/85.7; 424/85.6; 424/85.1; 424/85.5; 514/44 R; 514/5.8; 514/7.7; 525/54.1

(58) Field of Classification Search
CPC ....... A61K 9/06; A61K 47/34; A61K 9/0019; A61K 9/0024; C08B 37/0021; C08G 83/003; C08L 101/16; B82Y 30/00
USPC ................ 424/85.2, 130.1, 184.1, 85.1, 85.4, 424/85.5, 85.6, 85.7, 94.1; 514/1.1, 44 R, 514/5.8, 7.7, 772.1; 525/54.1
See application file for complete search history.

(56) References Cited

U.S. PATENT DOCUMENTS 6,388,047 B1  5/2002  Won et al.
6,491,061 B1  12/2002  Lopez et al.
(Continued)

FOREIGN PATENT DOCUMENTS

WO    WO 98/00170    *  1/1998

OTHER PUBLICATIONS

Cloninger ("Biological applications of dendrimers" in current Opinion in Chemical Biology, 2002, 6: 742-748).*

(Continued)

*Primary Examiner* — Blessing M Fubara
(74) *Attorney, Agent, or Firm* — Lathrop & Gage LLP; Brian C. Trinque

(57) ABSTRACT

Multifunctional polymers are disclosed having a smart segment and a biodegradable segment. Advantageously, the biodegradable segment includes a hydrophilic segment and a hydrophobic segment. Embodiments include combining the multifunctional polymeric material with a biologically active substance in an aqueous loading environment and administering the composition as a drug delivery vehicle to a human subject.

14 Claims, 15 Drawing Sheets

(51) Int. Cl.
| | |
|---|---|
| A61K 45/00 | (2006.01) |
| A61K 39/395 | (2006.01) |
| A61K 39/00 | (2006.01) |
| A61K 38/21 | (2006.01) |
| A61K 48/00 | (2006.01) |
| A61K 38/22 | (2006.01) |
| A61K 38/00 | (2006.01) |
| A61K 38/18 | (2006.01) |
| C08G 63/91 | (2006.01) |
| C08B 37/02 | (2006.01) |
| C08G 83/00 | (2006.01) |
| A61K 47/34 | (2006.01) |
| A61K 9/06 | (2006.01) |
| B82Y 30/00 | (2011.01) |
| C08L 101/16 | (2006.01) |
| A61K 9/00 | (2006.01) |

(56) References Cited

U.S. PATENT DOCUMENTS

2002/0068087 A1* 6/2002 Marchant ............... 424/486
2002/0146830 A1* 10/2002 Esuvaranathan et al. ..... 435/458

OTHER PUBLICATIONS

Esfand and Tomalia ("Polyamidoamine (PAMAM) dendrimers: from biomimicry to drug delivery and biomedical applications" in DDT vol. 6, No. Apr. 2001, 427-436).*

Caponetti, et al., "Microparticles of Novel Branched Copolymers of Lactic Acid and Amino Acids: Preparation and Characterization", Journal of Pharmaceutical Sciences 1999, vol. 88, pp. 136-141.

Klok, et al., "Self-Assembling Biomaterials: L-Lysine-Dendron-Substituted Cholesteryl-(L-lactic acid)", Marcromolecules 2002, vol. 35, pp. 6101-6111.

Jeong, et al., "Biodegradable Block Copolymers as Injectable Drug-Delivery Systems", Nature 1997, vol. 388, pp. 860-862.

Jeong, et al., "Poly(L-lysine)-g-poly(D,L-lactic-co-glycolic acid) Micelles for Low Cytotoxic Biodegradable Gene Delivery Carriers", Journal of Controlled Release 2002, vol. 82, pp. 159-166.

Kissel, et al., "Parenteral Protein Delivery Systems Using Biodegradable Polyesters of ABA Block Structure, Containing Hydrophobic poly(lactide-co-glycolide) A Blocks and Hydrophilic poly(ethylene oxide) B Blocks", Journal of Controlled Release 1996, vol. 39, pp. 315-326.

Gref, et al., "The Controlled Intravenous Delivery of Drugs Using PEG-Coated Sterically Stabilized Nanospheres", Advanced Drug Delivery Reviews 1995, vol. 16, pp. 215-233.

Gref, et al., "'Stealth' Corona-core Nanoparticles Surface Modified by Polyethylene Glycol (PEG): Influences of the Corona (PEG Chain Length and Surface Density) and of the Core Composition of Phagocytic Uptake and Plasma Protein Adsorption", Colloids and Surfaces B: Biointerfaces 2000, vol. 18, pp. 301-313.

Kurisawa, et al., "Modulated degradation of hydrogels with thennorespunsive network in relation to their swelling behavior", Macromolecular Chemistry and Physics 1998, vol. 199, pp. 705-709.

Kurisawa, et al., "Modulated degradation of dextran hydrogels grafted with poly(N-isopropylacrylamide-co-N,N-dimethylacrylamide) in response to temperature", Macromolecular Chemistry and Physics 1999, vol. 199, pp. 2613-2618.

Cao et al., "Delivering neuroactive molecules from biodegradable microspheres for application in central nervous system disorders", Biomaterials 1999, vol. 20, pp. 329-339.

Stile, et al. "Synthesis and characterization of injectable poly(N-isopropylacrylamide)-based hydrogels that support tissue formation in vitro", Macromolecules 1999, vol. 32, pp. 7370-7379.

Zhang, et al. "Synthesis and characterization of biodegradable network hydrogels having both hydrophobic and hydrophilic components with controlled swelling behavior", Journal of Polymer Science Part a-Polymer Chemistry 1999, vol. 37, pp. 4554-4569.

Klok, HA, et al. "Self-assembling biomaterials: L-lysine-dendron-substituted cholesteryl-(L-lactic acid)n", Macromolecules 2002, vol. 35, pp. 6101-6111.

Zhu, et al. "Thermosensitive aggregates self-assembled by an asymmetric block copolymer of dendritic polyether and poly(N-isopropylacrylamide)", European Polymer Journal 2002, vol. 38, pp. 2503-2506.

Yoshida, et al. "Newly designed hydrogel with both sensitive thermoresponse and biodegradability", Journal of Polymer Science Part A-Polymer Chemistry 2003, vol. 41, pp. 779-787.

Choi, et al. "Poly(ethylene glycol)-block-poly(L-lysine) dendrimer: Novel linear polymer/dendrimer block copolymer forming a spherical water-soluble polyionic complex with DNA", Bioconjugate Chemistry 1999, vol. 10, pp. 62-65.

Choi et al. "Synthesis of a barbell-like triblock copolymer, poly(L-lysine) dendrimer-block-poly(ethylene glycol)-block-poly(L-lysine) dendrimer, and its self-assembly with plasmid DNA", Journal of the American Chemical Society 2000, vol. 122, pp. 474-480.

Lowe, et al. (1998). "Partially fluorinated thermally responsive latices of linear and crosslinked copolymers" Journal of Polymer Science Part B-Polymer Physics 1998, vol. 36, pp. 2141-2152.

Lowe, et al. "Interactions of thermally responsive polyelectrolyte latices with low molar mass organic molecules studied by light scattering", Macromolecules 1998, vol. 31, pp. 1590-1594.

Lowe, et al. "Thermal and rheological properties of hydrophobically modified responsive gels", Macromolecular Chemistry and Physics 1999, vol. 200, pp. 51-57.

Lowe, et al. "Hydrophobically modified responsive polyelectrolytes", Langmuir 1999, vol. 15, pp. 4259-4265.

Lowe, TL, et al. (1999). "Interactions of drugs and spin probes with hydrophobically modified polyelectrolyte hydrogels based on N-isopropylamylamide", Polymer 1999, vol. 40, pp. 2595-2603.

Lowe, et al."Effect of hydrophobicity of a drug on its release from hydrogels with different topological structures", Journal of Applied Polymer Science 1999, vol. 73, pp. 1031-1039.

Dijk-Wolthuis, et al. (1997). "A new class of polymerizable dextrans with hydrolyzable groups: Hydroxyethyl methacrylated dextran with and without oligolactate spacer", Polymer 1997, vol. 38, pp. 6235-6242.

Dijk-Wolthuis, et al. "Degradation and release behavior of dextran-based hydrogels", Macromolecules 1997, vol. 30, pp. 4639-4645.

* cited by examiner

MULTI-FUNCTIONAL POLYMERIC MATERIALS AND THEIR USES

CROSS REFERENCE TO RELATED APPLICATION

This application is a divisional of U.S. application Ser. No. 10/807,510, filed Mar. 24, 2004, which claims priority from Provisional Patent Application No. 60/457,499, filed Mar. 24, 2003; Provisional Patent Application No. 60/466,966, filed May 1, 2003; and Provisional Patent Application No. 60/519,796, filed Nov. 14, 2003. The entire disclosures of each of the Patent Applications are hereby incorporated by reference.

FIELD OF THE DISCLOSURE

The present invention relates to multifunctional polymeric materials and their uses, in particular, the present invention relates to biologically responsive and biodegradable materials and their use as drug delivery vehicles, systems for gene therapy, scaffolds for tissue generation, biosensors, and bioseparation materials.

BACKGROUND

The costs associated with drug development are enormous. Improving the effectiveness of existing drug therapies has led to the design of new materials for drug delivery. For example, many protein drugs, such as nerve growth factor (NGF), have attracted growing interests for the treatment of neurodegenerative disorders, such as Alzheimer's disease. However, the uses of these drugs are still hampered by a lack of an effective route and method of delivery. This is partly because these protein drugs have very short half-lives, have difficultly crossing biological barriers, and are easily metabolized at other tissue sites. In addition, current available drug delivery systems can not achieve targeted and long-term drug release while at the same time responding to environmental changes (such as temperature, pH, etc.) which are caused by many disorders in organs and blood vessels.

Biodegradable polymers play an important role in drug delivery. Because these polymers degrade after a certain period of time, sustained drug release can be enhanced and surgical removal after drug depletion can be avoided. However, many biodegradable polymers have disadvantages in requiring organic solvents for drug loading thereby limiting the selection of drugs that are not adversely affected, i.e. denaturation of protein drugs, by such solvents. Biodegradable polymers also suffer from inconsistent drug release kinetics and lack of response to physiological changes in living organisms. Bioresponsive polymers are another class of polymers widely studied, especially as devices for the delivery of physiological unstable agents, such as protein drugs including growth factors. This class of materials is responsive to physical, chemical, or biological stimuli. However, bioresponsive polymers have problems in non-biodegradability and non-sustained drug release.

Accordingly, a continuing need exists for the development of new materials that can be tuned to biologically activity and precise drug delivery vehicles and for other related uses.

SUMMARY OF THE DISCLOSURE

An advantage of the present invention is multifunctional polymeric materials. These materials can advantageously, without limitation, be tuned for precise control and prolonged delivery of therapeutic agents. These materials can also advantageously be used as supporting structures in biological organisms, such as scaffolds for tissue generation.

Additional advantages, and other features of the present invention will be set forth in the description which follows and in part will become apparent to those having ordinary skill in the art upon examination of the following or may be learned from the practice of the present disclosure. The advantages may be realized and obtained as particularly pointed out in the appended claims.

According to the present invention, the foregoing and other advantages are achieved in part by a polymeric material comprising a smart segment and a biodegradable segment. Such a multifunctional polymeric material advantageously has a biodegradable segment that includes a hydrophobic segment and a hydrophilic segment, which can be hydrolytically or enzymatically degradable. The present invention advantageously combines the properties of a smart polymer, e.g., a material that is biologically, chemically, or physically responsive to an external stimulus, with that of a biodegradable polymer thereby forming materials that are particularly suited for use in biological organisms.

Another advantage of the present invention is the use of such multifunctional polymeric materials with a substance, e.g., a biologically active or an inert substance, for use in biological organisms. By controlling the chemistry of the segments of the multifunctional polymeric material, aqueous loading of biologically active substance can be achieved in preparing a composition with the multifunctional polymeric material. These and other compositions including the multifunctional polymeric material can be administered to a subject, such as a human, and used as a delivery vehicle or as a support structure within the subject.

Additional advantages of the present invention will become readily apparent to those skilled in this art from the following detailed description, wherein only the preferred embodiments of the present invention are shown and described, simply by way of illustration but not limitation. As will be realized, the invention is capable of other and different embodiments, and its several details are capable of modification in various obvious respects, all without departing from the spirit of the present invention. Accordingly, the drawings and description are to be regarded as illustrative in nature, and not as restrictive.

DESCRIPTION OF THE DRAWINGS

The various features and advantages of the present invention will become more apparent and facilitated by reference to the accompanying drawings, submitted for purposes of illustration and not to limit the scope of the invention.

DETAILED DESCRIPTION OF THE DISCLOSURE

Figure 1:
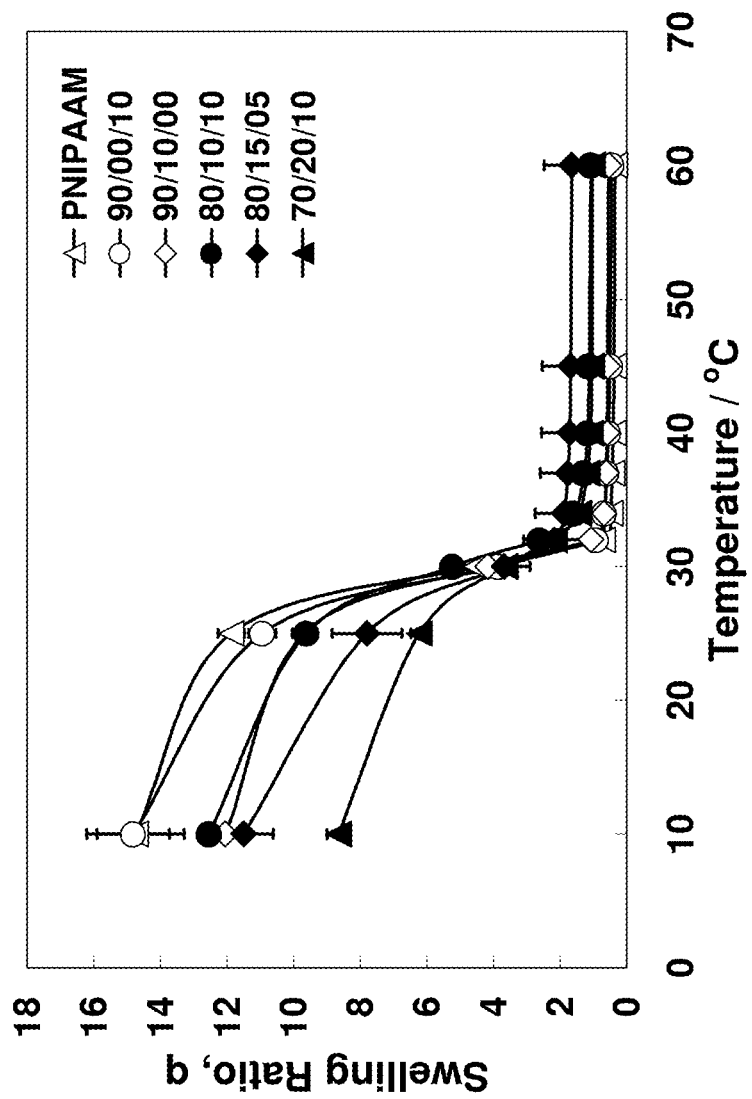
FIG. 1 is a chart showing the swelling ratios for a series of hydrogels comprising a PNIPAAM segment, a PLLA segment and a Dextran segment in accordance with one aspect of the present invention. In particular, the chart shows thermoresponsive properties of the hydrogels by measuring swelling ratios as a function of temperature from 10 to 60° C. after equilibrium for 1 day at each temperature interval in PBS solvent (pH of about 7.4).

The present invention stems from the discovery that certain properties of individual polymers can be combined to form materials that are smart, i.e. respond to stimuli, and biodegradable in vivo. It was discovered, after investigation and experimentation, that materials which combine a smart segment with a degradable hydrophobic and/or hydrophilic segment can be used for drug delivery and/or as a support for tissue growth. A segment is considered to be a covalently bound portion of the material and can have a plurality of polymerized units. For example, a segment can include several polymerized monomer units up to about several thousand polymerized monomer units. These segments can have any length and any molecular weight, however it is preferred that each segment has a molecular weight that is roughly large enough to approximate a desired property expected for that polymer segment. In particular, each segment can have a number or weight average molecular weight of about 100 to about 800,000, and it is preferred that the segments have a number average molecular weight of about 500 to about 80,000. Although it is common to refer to polymers and segment by the name of the monomer or monomers from which it can be derived, the segments and polymers described herein are not limited to any particular method of preparing the segments or polymers.

In one aspect of the present invention, the smart segment is responsive to an external stimulus, such as a chemical, biological, or physical stimulus, and sharply changes at least one of its physical properties in response to the stimulus. For example, bioresponsive polymers respond to physical, chemical, or biological stimuli, such as temperature, pH, ionic strength, magnetic field, electrical field, pressure, light, enzyme, receptor, glucose, etc. by altering their swelling behavior, permeability or mechanical strength. Specifically, thermo-responsive polymers respond to environmental temperature changes with structural and morphological changes by absorbing or expelling water. Poly(N-isopropylacrylamide) (PNIPAAm), a representative of thermo-responsive polymers, shows a lower critical solution temperature (LCST) around 32° C., close to mammalian body temperature. Crosslinked PNIPAAm hydrogels experience a sharp volume phase transition at the LCST, changing between highly hydrophilic at temperatures below the LCST and highly hydrophobic above the LCST. Through copolymerizing with other hydrophilic or hydrophobic monomers, the physical, chemical, and mechanical properties of PNIPAAm-based hydrogels can be tuned, adjusted and controlled to respond to different thermal and biological stimuli.

Other examples of smart polymers include poly(N-alkylacrylamide) and its derivatives, such as poly(N-isopropylmethacrylamide) and poly(N-n-propylacrylamide), poly(ethylene oxide)-polypropylene oxide)-poly(ethylene oxide), poly(ethylene oxide)-co-poly(L-lactic acid), and elastin-like polypeptides.

However, responsive polymers when used alone have problems in non-biodegradability. Thus combining a smart polymer segment with a biodegradable polymer segment results in a material considerably more versatile than the individual materials. By combining both bioresponsive and biodegradable polymers, drug delivery systems can be fashioned which are both biodegradable and responsive to physiological stimuli. In one embodiment of the present invention, a multifunctional polymeric material is provided comprising a smart segment and a biodegradable segment, wherein the biodegradable segment includes a hydrophobic segment and a hydrophilic segment.

A number of natural and synthetic biodegradable polymers are known. Some have been studied, including polyesters, such as polylactides (PLA), poly(L-lactic acid), poly(D,L-lactic acid), poly(lactide-co-glycolides) (PLGA), biotinylated poly(ethylene glycol-block-lactic acid), poly(alkylcyanoacrylates) and poly(epsilon-caprolactone); polyanhydrides, such as poly(bis(p-carboxyphenoxy) propane-sebacic acid) (PCPP-SA), polyorthoesters, polyphosphoesters, polyphosphazenes, polyurethanes, and poly(amino acids), polysaccharides, such as dextran, in the forms of microcapsules, microparticles, nanoparticles, hydrogels and micelles. All of such biodegradable polymers are contemplated in the present invention as segments of a multifunctional material.

The forgoing polymers degrade by hydrolytic or enzymatic cleavage of the backbone and, hence, can avoid surgical removal after drug depletion. The degradation properties of the polymers depend on their chemical composition, tacticity, crystallinity, molar mass, morphology, size and shape, and also pH and temperature. The chemical and physical properties of biodegradable polymers are known to influence the drug release patterns, and the release kinetics of the loaded drugs are controlled by both drug diffusion and polymer degradation. However, many currently investigated biodegradable polymers have the following four major disadvantages, 1) encapsulation of protein drugs involves organic solvents which may cause protein denaturation and increase of immunogenicity or toxicity; 2) drug release kinetics are inconsistent that may economically and therapeutically cause waste of the drugs and other adverse effects; 3) plasma life time of the biodegradable polymers is low because of their rapid capture by the mononuclear phagocyte system (MPS) cells; and 4) biodegradable polymers lack response to physiological changes.

In order to avoid some of the problems associated with hydrophobic biodegradable polymers, the present invention contemplates providing multifunctional polymeric materials with a hydrophilic biodegradable segment together with the hydrophobic segment in an embodiment of the present invention. For example, Kissel et al. (Kissel et al. J. Controlled Release 1996, 39:315-326) showed that PLGA triblock copolymers with hydrophilic poly(ethylene oxide) (PEO) in the center, or PLGA grafted onto hydrophilic backbones such as dextran or charge-containing dextran-sulfate as well as poly(vinyl alcohol), provide high hydrophilic protein drug encapsulation efficiency and a continuous release of proteins instead of polyphasic release for PLGA copolymer alone over several weeks due to a rapid water uptake and swelling of the polymers. Nanospheres prepared from diblock copolymers of PLGA and PEO were effective to reduce plasma protein adsorption, and showed extended blood circulation times and reduced liver accumulation in mice, depending on the molar mass and density of the PEO component. (Gref et al. Adv. Drug Delivery Rev. 1995; 16:215-233; Gref et al. Colloids and Surfaces B: Biointerfaces 2000, 18:301-313) The present invention contemplates forming multifunctional polymeric materials containing hydrophobic-hydrophilic segments from such hydrophobic and hydrophilic polymers or monomer units thereof.

Another approach to affect the degradation rates and protein release rates includes coating or grafting hydrophobic materials, e.g. PLA and PLGA micro/nanoparticles, with poly-L-lysine (PLL) due to the PLL's charge, hydrophilicity and targeting capability. For example, Langer's group (Caponetti et al. J. Pharm. Sci. 1999, 88:136-141) synthesized microparticles composed of poly(L-lactic acid-co-L-lysine) grafted with PLL and demonstrated that the polymers with the PLL side chains significantly increased the release of rhodamine B compared to those without the PLL side chains. Park and co-workers (Jeong et al. J. Controlled Release 2002, 82:159-166) reported that PLGA grafted with PLL micelles showed 10 times higher transfection efficiency and 5 times less cytotoxicity than PLL. The present invention contemplates the use of such coating and grafting techniques in providing hydrophilic-hydrophobic degradable segments.

The polymeric materials of the present invention can have a variety of structures, such as a hydrogel structure, a dendritic structure and other structures such as a nanoparticle, nanosphere, nanoshell, micelle, core-shell, multi-core shell, multi-layered, nanogel, microparticle, microsphere, microgel, block, branched, hyperbranched, hybrid, tree-like, comb-like, brush, grafting, vesicle, coil, global, coil-coil, coil-global, rod, membrane, film, coating, self-assembly, cyclic, microconduit, microchannel, nanochannel, nonporous, tube, microtube, nanotube, porous, semi-interpenetrating network, cross-linked, or some highly networked structure.

Hydrogels are three-dimensional crosslinked polymer networks that swell in an aqueous environment by absorbing large amounts of water while maintaining their structure. Due to their high water content, biocompatibility, and unique mechanical properties, hydrogels have attracted wide interests in biomedical applications such as drug delivery and tissue engineering. Environmental-sensitive hydrogels prepared in accordance with the present invention can control drug release by changing their structures in response to environmental stimuli, such as temperature, pH, electrical signal, ionic strength, etc. Covalently and non-covalently (physically) crosslinked temperature-sensitive, biodegradable gels are preferred materials as hydrogels.

In one embodiment of the present invention, hydrogels were prepared as copolymeric networks composed of N-isopropylacrylamide (NIPAAM) or a derivative thereof as a smart or responsive component; poly(L-lactic acid) (PLLA) or a derivative thereof as a hydrolytically degradable and hydrophobic component; and dextran or a derivative thereof as an enzymatically degradable and hydrophilic component. The components or segments can be of any length including from about 3 monomer units to about 10,000 monomer units, e.g. about 3 to 5,000 units. In a preferred embodiment, the hydrogel comprises approximately 40% to 99% molarity, e.g., about 70-95% molarity, of poly(N-isopropylacrylamide) as the smart segment, and approximately 1% to 40% molarity, e.g., about 3-28% molarity, of polylactic acid and approximately 0% to 59% molarity, e.g., about 0-27% molarity, of dextran as the biodegradable segment. The material or segments can further comprise other monomer units to adjust the materials properties. For example, the hydrogel can also include anionic (acrylic acid) and cationic (acrylic amine) units for increasing pH and ionic strength sensitivity of the gel.

PNIPAAM-PLLA-Dextran hydrogels were thermo-responsive showing a lower critical solution temperature (LCST) at approximately 32° C., and their swelling properties strongly depended on temperature changes, the balance of the hydrophilic/hydrophobic components and the degradation of the PLLA component. The degradation of the hydrogels caused by hydrolytic cleavage of ester bonds in PLLA component, was faster at 25° C., below the LCST than at 37° C., above the LCST, as determined by ATR-FTIR and weight loss measurement. Due to their multifunctional properties, the designed hydrogels show practical use in biomedical applications including drug delivery, gene therapy, tissue engineering, biosensor and bioseparation.

The multifunctional polymeric materials of the present invention can also be in the form of dendrimeric structures. Dendrimers are defined by regular, highly branched segments leading to a relatively monodisperse, tree-like or generational structure. Dendrimers possess three distinguishing architectural features: the core; the interior area containing branch upon branch of repeat units or generations with radial connectivity to the core; and an exterior or surface region of terminal moieties attached to the outermost generation. A dendrimer can be defined into a multitude of structures by tuning these three architectural components. Dendrimers that are highly branched and reactive three-dimensional macromolecules have become increasingly important in biomedical applications due to their high degree of molecular uniformity, narrow molecular weight distribution, specific size and intriguing structural properties such as internal voids and cavities, and a highly functional terminal surface. The spatially arranged functional groups can react with a variety of molecules, for example, hydrophilic molecules such as PEO to increase their blood circulation times, contrast agents for use in magnetic resonance imaging (MRI), and targeting molecules to localize to desired tissue sites.

Currently available dendrimers contain benzyl ether, propyleneimine, amidoamine, L-lysine, ester and carbosilane dendritic segments. Among them, cationic polyamidoamine (PAMAM) dendrimers have been widely studied and were reported to mediate high levels of gene transfection in a wide variety of cells, depending on the dendrimer-DNA ratio, the size and especially the flexibility of the dendrimers. PAMAM dendrimers are considered targeted delivery systems, and can enhance accumulation within certain tumor microvasculature, increase extravasation into tumor tissue. Poly(L-lysine) (PLL) dendrimer is another polycationic dendrimer containing a large number of surface amines and considered to be capable of the electrostatic interaction with polyanions, such as nucleic acids, proteoglycans found in extracellular matrix and phospholipids of the cell membrane. These polymers can localize drugs to the targeted membranes and increase BBB permeability several-fold.

However, polycationic dendrimers still have in vivo toxicity problems and are resistant to degradation in the body and are thus less suitable for drug delivery. To improve the cytotoxicity of PAMAM dendrimers, the cationic amine terminal groups of the dendrimers can be replaced with anionic carboxylate terminal groups. The present inventive materials address some of the disadvantages of dendrimer structures prepared from individual components by combining smart and degradable segments as arms, branches, or dendrons of a dendrimeric structure. Such dendrimeric materials can be prepared by coupling a thermoresponsive polymer segment with a biodegradable polymer segment in a chemical bond forming reaction.

In one embodiment of the present invention, a dendrimer is prepared comprising a poly(N-isopropylacrylamide) segment or derivative thereof as a smart or responsive component, a poly(lysine) segment or derivative thereof as a polyionic (polycationic or polyanionic) component, and a poly (lactic acid) segment or derivative thereof as a biodegradable component. The poly(N-isopropylacrylamide) segment or derivative thereof can have a number average molar mass of between about 1000 and about 600,000 g·mol$^{-1}$, the poly (lysine) segment or derivative thereof can have a number average molar mass of between about 150 and about 600,000 g·mol$^{-1}$, and the poly(lactic acid) segment or derivative thereof can have a number average molar mass of between about 100 and about 600,000 g mol$^{-1}$. The dendrimers can have about 1 to about 5 dendrons, and each dendron can have about 1 to about 12 generations of poly(lysine) or other polycationic (or polyanionic) segments. In a preferred embodiment, the poly(lysine) segment or derivative thereof is a poly (L-lysine) or derivative thereof and the poly(lactic acid) segment or derivative thereof is a poly(L-lactic acid) or a derivative thereof.

In addition, dendrimers can also be prepared as nanoparticles. It is believed that particles having a size of about 1 nm to 1000 nm hold a significant advantage in transporting drugs across the blood-brain barrier. Drugs are loaded into the nanoparticles by adsorption, entrapment and covalent attachment, and released from the nanoparticles by desorption, diffusion, polymer erosion or some combination of any or all the above mechanisms. In vitro and in vivo experiments show that nanoparticles can have long blood circulation times and a low reticuloendothelial system (RES) uptake when they are stabilized by dextran and coated with polysorbate 80. They are able to interact with the brain blood vessel endothelial cells of mice, and then be taken up by these cells by endocytosis. Dendrimers are believed to have greater potency in delivering drugs across the BBB.

The multifunctional polymeric material of the present invention can be used as supporting structures, delivery vehicles or for any other purpose in biological systems or organisms. Although the multifunctional polymeric materials of the present invention are suitable for such applications, they are not limited thereto. In one aspect of the present invention, a multifunctional polymeric material is combined with a substance to comprise a composition. The substance can be biologically active or inert. In a preferred embodiment, the substance is a biologically active substance. A biologically active substance refers to any agent that is biocompatible and capable of producing an effect. Such substances include vitamins, antiperspirants, suntan lotions, drugs, etc. A drug refers to any substance used in the prevention, diagnosis, alleviation, mitigation, treatment, or cure of disease. A drug also refers to those substances that affect the structure or function of a biological system, such as the human body.

The multifunctional materials of the present invention can be combined with a wide variety of biologically active substances. Such biologically active substances comprise a protein, peptide, gene, enzyme, receptor, vaccine, antibody, hormone, antibiotic, drug, interferon consensus, interleukin, erythropoietin, granulocyte-colony stimulating factor (GCSF), stem cell factor (SCI), leptin (OB protein), interferon (alpha, beta, gamma), antibiotics, such as ciprofloxacin, amoxycillin, lactobacillus, cefotaxime, levofloxacin, cefipime, mebendazole, ampicillin, lactobacillus, cloxacillin, norfloxacin, timidazole, cefpodoxime, proxctil, azithromycin, gatifloxacin, roxithromycin, cephalosporin, anti-thrombogenics, such as aspirin, ticlopidine, sulfinpyrazone, heparin, warfarin, growth factors, such as differentiation factors, hepatocyte stimulating factor, plasmacytoma growth factor, brain derived neurotrophic factor (BDNF), glial derived neurotrophic factor (GDNF), neurotrophic factor 3 (NT3), fibroblast growth factor (FGF), transforming growth factor (TGF), platelet transforming growth factor, milk growth factor, endothelial growth factors (EGF), endothelial cell-derived growth factors (ECDGF), alpha-endothelial growth factors, beta-endothelial growth factor, neurotrophic growth factor, nerve growth factor (NGF), vascular endothelial growth factor (VEGF), 4-1 BB receptor (4-1BBR), TRAIL (TNF-related apoptosis inducing ligand), artemin (GFRalpha3-RET ligand), BCA-1 (B cell-attracting chemokine1), B lymphocyte chemoattractant (BLC), B cell maturation protein (BCMA), brain-derived neurotrophic factor (BDNF), bone growth factor such as osteoprotegerin (OPG), bone-derived growth factor, megakaryocyte derived growth factor (MGDF), keratinocyte growth factor (KGF), thrombopoietin, platelet-derived growth factor (PGDF), megakaryocyte derived growth factor (MGDF), keratinocyte growth factor (KGF), platelet-derived growth factor (PGDF), bone Morphogenetic protein 2 (BMP2), BRAK, C-10, Cardiotrophin 1 (CT1), CCR8, anti-inflammatory agents, such as paracetamol, salsalate, diflunisal, mefenamic acid, diclofenac, piroxicam, ketoprofen, dipyrone, acetylsalicylic acid, antimicrobials, amoxicillin, ampicillin, cephalosporins, erythromycin, tetracyclines, penicillins, trimethprim-sulfamethoxazole, quniolones, amoxicillin, clavulanatf, azithromycin, clarithromycin, anti-cancer drugs, aliteretinoin, altertamine, anastrozole, azathioprine, bicalutamide, busulfan, capecitabine, carboplatin, cisplatin, cyclophosphamide, cytarabine, doxorubicin, epirubicin, etoposide, exemestane, vincristine, vinorelbine, hormones thyroid stimulating hormone (TSH), sex hormone binding globulin (SHBG), prolactin, luteotropic hormone (LTH), lactogenic hormone, parathyroid hormone (PTH), melanin concentrating hormone (MCH), luteinizing hormone (LHb), growth hormone (HGH), follicle stimulating hormone (FSHb), haloperidol, indomethacin, doxorubicin, epirubicin, amphotericin B, Taxol, cyclophosphamide, cisplatin, methotrexate, pyrene, amphotericin B, anti-dyskinesia agents, Alzheimer vaccine, antiparkinson agents, ions, edetic acid, nutrients, glucocorticoids, heparin, anticoagulation agents, anti-virus agents, anti-HIV agents, polyamine, histamine and derivatives, cystineamine and derivatives, diphenhydramine and derivatives, orphenadrine and derivatives, muscarinic antagonist, phenoxybenzamine and derivatives, protein A, streptavidin, nucleic acids (DNA, RNA), amino acid, beta-galactosidase, methylene blue, protein kinases, beta-amyloid, lipopolysaccharides, eukaryotic initiation factor-4G, tumor necrosis factor (TNF), tumor necrosis factor-binding protein (TNF-bp), interleukin-1 (to 18) receptor antagonist (IL-Ira), granulocyte macrophage colony stimulating factor (GM-CSF), novel erythropoiesis stimulating protein (NESP), thrombopoietin, tissue plasminogen activator (TPA), urokinase, streptokinase, kallikrein, insulin, steroid, acetylsalicylic acid, acetaminophen, analgesic, anti-tumor preparation, anti-cancer preparation or medication, anti-proliferative preparation or pro-apoptotic preparation.

In one aspect of the present invention, compositions are prepared with the multifunctional polymeric materials. An advantage of the present materials is the loading of biologically active substances in an aqueous environment. Loading drugs, for example, in an aqueous phase with high loading efficiency can avoid instability and denaturation of sensitive drugs during common formulation process and is an advantage over delivery vehicles that ordinarily require organic solvents. In practicing one aspect of the present invention, biologically active substance are loaded in a multifunctional polymeric material by combining a multifunctional polymeric material with a biologically active substance in an aqueous medium to form a composition comprising the polymeric material with the biologically active substance. In an embodiment of the present invention, the biologically active substance comprises approximately 40 wt % of the composition.

The compositions comprising multifunctional materials and active or inert substances can be administered to a biologically system or organism. In one embodiment of the present invention, a composition comprising a multifunctional polymeric material and a biologically active substance is administered to a subject in need of receiving such a composition. As used herein, a subject is any living organism including a human and administrating to the subject comprises, without limitation, inserting, injecting, implanting, delivering, injecting, and infusing the composition in or to the subject. The administration can also be local administration, oral administration, intraperitioneal administration, systemic administration, intravenous administration, transdermal administration, intramuscular administration, intra/extravascular administration, intra-arterial administration, intrathecal administration, intracranial administration, conjunctival administration, intra-amniotic administration, chemotherapeutic administration, rectal administration, ophthalmic administration, percutaneous administration, or subcutaneous administration. In a preferred embodiment of the present invention, a human subject is administered a composition comprising a multifunctional polymeric material and a biologically active substance wherein the biologically active substance is administered to have a concentration of up to approximately 1,000 mg ml$^{-1}$.

In another aspect of the present invention, the compositions comprising the multifunctional polymeric material and a biologically active substance can be administered as a drug delivery or gene therapy vehicle to a subject in need thereof. The compositions can release the biologically active substance in a controlled sustained manner for a few hours to up to several days and even years and up to a release rate of about 0-10 g/day, e.g. about $1 \times 10^{-6}$ to about 1 g/day.

In another aspect of the present invention, the compositions comprising the multifunctional polymeric material can be used as 2-D or 3-D scaffolds for tissue engineering. The compositions can be used to seed cells inside or on the surface to promote cell growth including cell adhesion, proliferation, and differentiation.

In another aspect of the present invention, the compositions comprising the multifunctional polymeric material can be used in the applications of drug delivery systems combining the functions of biosensors. The compositions can include drugs such as insulin, or enzyme, such as glucose oxidase, to oxidize glucose into gluconic acid, which decreased the pH in the surrounding area and caused expanding or shrinking of the polymers, so that the incorporated insulin can be automatically release in response to the local glucose concentration.

In another aspect of the present invention, the compositions comprising the multifunctional polymeric material can be used in bioseparation. The compositions can conjugate with compounds, e.g. antibodies, to bind favorable molecules in aqueous solutions. When the compositions are heated above its LCST, it collapses with the favorable molecules. The favorable molecules can be obtained through reswelling the molecule-bound compositions in aqueous solvents.

It is believed that smart and biodegradable dendrimers containing thermoresponsive poly(N-isopropylacrylamide) (PNIPAAM), hydrophobic and biodegradable poly(L-lactic acid) (PLLA), and poly(L-lysine) (PLL) dendrons can provide targeted and sustained delivery of therapeutic agents, e.g. nerve growth factor (NGF) across biological barriers, e.g. blood-retinal barrier (BRB) and blood-brain barrier (BBB). The examples provided below support this use. In designing the present dendrimer, PNIPAAM is chosen as a thermo-targeting moiety due to its phase transition at the LCST. When the LCST of the PNIPAAM is modified by PLLA and PLL as described below to the temperature higher than body temperature 37° C. but lower than 42° C. as used routinely in clinical hyperthermia, the resulting dendrimers are soluble in the blood stream after systemically injection and the PNIPAAM can act as a hydrophilic component to increase the blood-circulation times of the dendrimers due to its inherently high mobile nature. When the brain is heated to 42° C. above the LCST, the dendrimers become hydrophobic and start to aggregate at the BBB and then can be taken up by the endothelial cells of the BBB so that they can increase the BBB permeability of the loaded NGF. This thermally targeting strategy can achieve a high concentration of the dendrimers at the BBB while the dendrimers is injected systematically at lower concentration. In addition, PNIPAAM can also provide an effective way to control the biodegradable mechanisms of the dendrimers to achieve desired drug release rate. In one aspect of the present invention, a pharmaceutical composition comprising a multifunctional polymer and a biologically active substance is administered to a subject, e.g., a human, and targeted to a region of therapeutic interest to release, by a sustained release or otherwise, the biologically active substance. The targeting can be carried out by thermal targeting, e.g., by using ultra-sound, radio frequency, heat pack, etc., or any other method or their equivalent at the region of interest.

PLLA was chosen due to its combination of hydrophobicity, biodegradability, and good mechanical strength. The hydrophobicity of the PLLA can decrease the LCST of the PNIPAAM but support the molecular structure. The biodegradability of the PLLA can achieve sustained NGF delivery. PLL dendron was chosen because of its excellent hydrophilic nature and great amount of terminal free amine groups. The hydrophilic nature of the PLL can increase the LCST of the PNIPAAM. The polyamine groups of the PLL can increase the BBB permeability of the NGF by passive adsorption through electrostatic interaction with negatively charged endothelial cells in the BBB. In order to increase the accumulation of the dendrimers at the BBB after cessation of hyperthermia which will cause resolubilization of the dendrimers due to reverse of the phase transition of the PNIPAAM, the polyamine groups of the PLL can be used to conjugate with transferrin or OX26 monoclonal antibody that can bind with transferrin-receptor that is endowed in the BBB. By this method, the smart and biodegradable dendrimers can localize the NGF at the BBB through dual thermal-affinity targeting, increase the plasma stability of the NGF through increasing their hydrophilicity and flexibility using PLL and PNIPAAM, and release the NGF for a long period of time by incorporating with biodegradable PLLA.

EXPERIMENTAL

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

1.0 Hydrogels

Multifunctional hydrogels with both thermoresponsive and biodegradable properties, were synthesized, and characterized. The hydrogels were copolymeric networks composed of N-isopropylacrylamide (NIPAAM) as a thermoresponsive component, poly(L-lactic acid) (PLLA) as a hydrolytically degradable and hydrophobic component, and dextran as an enzymatically degradable and hydrophilic component. Due to their multifunctional properties, the designed hydrogels are suitable for biomedical applications including drug delivery and tissue engineering.

1.1 Synthesis of Hydrogel NIPAAM-PLLA-DEXTRAN

To prepare the hydrogels, PLLA and dextran were chemically modified to have unsaturated functional groups, which can undergo crosslinking. The synthesis of the hydrogels included three steps: (1) modified PLLA as a diacrylate macromer by conversion of —COOH end groups of PLLA to —OH end groups, then conversion of these —OH end groups to acrylate units, (2) modified dextran as a dextran allyl isocyanate (DAI) macromer, and (3) chemically crosslinked NIPAAM, PLLA diacrylate macromer, and DAI macromer to form copolymeric hydrogels.

1.1.1 Materials:

NIPAAM was obtained from Aldrich Chemicals (Milwaukee, Wis.), purified by recrystallization from hexane. PLLA (MW 2,000 g·mol$^{-1}$) was purchased from Polysciences (Warrington, Pa.). Dextran (MW 1,500 g·mol$^{-1}$) was obtained from Fluka Chemika (Switzerland). Dichloromethane (MC), dimethyl-formamide (DMF), 2-propanal, hexane, and N,N, N',N'-tetramethylethylenediamine (TEMED) were from Aldrich Chemicals (Milwaukee, Wis.). 1-hydroxybenzotrazole (HOBT), 1,3-dicyclohexyl-carbodiimide (DCC), 2-aminoethanol, acryloyl chloride, allyl isocyanate (AI), triethylamine (Et$_3$N), 2,2'-azobis(2-methylpropionitrile) (AIBN), and N'—N'-methylene-bis-acrylamide (BA) were obtained from Sigma Chemicals (St. Louis, Mo.). The above chemicals were used as received unless otherwise indicated. Deionized distilled water was used in the experiments.

1.1.2 Synthesis of PLLA Macromer.

The synthesis process of PLLA diacrylate macromer from PLLA was modified from the method used by Zhang and coworkers. (Zhang, et al. J. Poly. Sci., Poly. Chem. 1999, 37, 4554-4569.) The experimental process involved three steps. (i) Obtaining activated PLLA. PLLA (4.0 grams, 2 mmol) was dissolved in the solvent mixture of MC and DMF (7:3 in volume ratio) under the purge of dry nitrogen in a round bottom flask at 0° C. HOBt (405 mg, 3 mmol) was then added and dissolved. DCC (619 mg, 3 mmol) was dissolved in a small volume of MC/DMF mixture and added into the flask. The mixture was allowed to proceed with continuous stirring for 2 h, the precipitated by-product was filtered out; and the filtrate was poured into a large excess of dry hexane to obtain the activated PLLA product. The activated PLLA was purified by dissolution and reprecipitation with MC and hexane; thereafter, it was dried under vacuum at room temperature overnight. The yield of this step of reaction was 64%. (ii) Obtaining PLLA diol. The dry activated PLLA was weighed and dissolved in MC/DMF (7:3) in a round bottom flask under dry nitrogen purge at room temperature. Calculated amount of 2-aminoethanol (200 mol % of activated PLLA molecules) was dissolved in a small volume of MC/DMF and added into the flask dropwise. The mixture was stirred for 4 h before the by-product was filtered and discarded. The filtrate was then poured into large excess of dry hexane, and PLLA diol product was purified by dissolution and re-precipitation with MC and hexane. Then, the product was dried under vacuum at room temperature overnight. The yield of this step of reaction was 76%. (iii) Obtaining PLLA acrylate macromer. To convert PLLA diol to PLLA acrylate macromer, the dry diol product was weighed and dissolved in MC/DMF solvent in a round bottom flask under the purge of dry nitrogen at 0° C. Calculated amount of Et$_3$N (Et$_3$N:PLLA diol=4:1 (mol/mol)) was added to the flask. Acryloyl chloride (acryloyl chloride: PLLA diol=4:1 (mol/mol)) was mixed with a small volume of MC/DMF and slowly added dropwise into the flask under continuous stirring. The reaction proceeded at 0° C. for 3 h and was brought to room temperature to continue for another 18 h. After reaction, the PLLA macromer product was obtained by pouring the mixture into large excess volume of dry hexane. The product was purified by dissolution and reprecipitation in MC and hexane, respectively, and dried under vacuum at room temperature overnight. The yield of this step of reaction was 93%.

1.1.3 Synthesis of Dextran Allyl Isocyanate Macromer.

Dextran (8 grams, 5.56 mmol) was dissolved in DMF in a round bottom flask under the purge of dry nitrogen at room temperature. Triethylamine (0.69 ml, 4.95 mmol) was added into the flask. Allyl isocyanate (4.36 ml, 49.5 mmol) was then mixed with a small volume of DMF and added slowly dropwise. The reaction was allowed to proceed for 2 h under stirring. DAI macromer product was collected by precipitating into large excess volume of 2-propanol. The precipitate was washed with 2-propanol several times and dried under vacuum at room temperature for 2 days. The yield of this reaction was 58%.

1.1.4 Synthesis of Hydrogel NIPAAM-PLLA-DEXTRAN.

The hydrogels were synthesized by free radical polymerization. Calculated amounts (1 gram in total) of PLLA diacrylate macromer, DAI macromer, and NIPAAM were dissolved sequentially in 4.5 ml DMF in a 50 ml volume beaker at ~65° C. Certain amount of crosslinking agent BA (4 mol % based on total amount of C=C functional groups in the NIPAAM, PLLA macromer, and DAI macromer) was then added and dissolved. Dry nitrogen was purged into the solution for about 30 min. AIBN (2 mol % of total C=C functional groups) was dissolved in 0.5 ml DMF and added into the beaker. Finally, TEMED (6.4 mol % of total C=C functional groups) was added before nitrogen purge was removed and the beaker was closed with Parafilm®. The polymerization was allowed to proceed at 65° C. for 4 h. The formed hydrogel were cut into two size discs with diameter of about 8 and about 3 mm and thickness of about 3 and about 1 mm, respectively. The disc-shaped gel samples were then washed in 50:50 (v/v) mixture of ethanol and deionized water for 24 h to remove the unreacted chemicals. The washing solutions were changed several times during the period. The washed samples were then dried in the air at room temperature for several days until no further weight loss could be detected. The larger samples were used for thermo-responsive, swelling and degradation studies. The smaller samples were used for NGF release, cell toxicity and neurite outgrowth studies. The illustrative structure of synthesized hydrogels is shown in Scheme 1.

Wherein R is a —CONHCH$_2$CH=CH$_2$ or H, and m and n integers from about 1 to several thousand. The NIPAAM segment can also have units of from about 10 to several thousand.

Nine hydrogels were synthesized in accordance with the above procedures with the following compositions shown in Table 1.

TABLE 1

Compositions and Yields of Hydrogels.
Monomer Feeding Molar Ratios

| Samples | NIPAAM | L-lactic acid unit in PLLA | Anhydroglucose unit in dextran | Yield ± S.D.[a] (%) |
|---|---|---|---|---|
| PNIPAAm | 100 | 0 | 0 | 87.92 ± 2.14 |
| 90/10/00 | 90 | 10 | 0 | 73.14 ± 0.52 |

TABLE 1-continued

Compositions and Yields of Hydrogels.
Monomer Feeding Molar Ratios

| Samples | NIPAAM | L-lactic acid unit in PLLA | Anhydroglucose unit in dextran | Yield ± S.D.[a] (%) |
|---|---|---|---|---|
| 90/00/10 | 90 | 0 | 10 | 40.68 ± 1.60 |
| 80/10/10 | 80 | 10 | 10 | 39.79 ± 1.45 |
| 80/15/05 | 80 | 15 | 5 | 50.57 ± 2.08 |
| 70/20/10 | 70 | 20 | 10 | 44.84 ± 1.26 |
| 70/10/20 | 70 | 10 | 20 | — |
| 60/30/10 | 60 | 30 | 10 | — |
| 93/05/02 | 93 | 5 | 2 | — |

[a]Standard deviation values are based on three syntheses

1.1.5 Hydrogel Characterization

1.1.5.1 Characterization of hydrogel NIPAAM-PLLA-DEXTRAN chemical structures.

ATR (Pike Technologies, Madison, Wis.) FTIR spectroscopy (Thermo Nicolet Avetar 370, Madison, Wis.) was used to obtain IR spectra of the samples. Before the measurements of IR absorbance, PLLA and its macromers, and dextran and its macromers, were dissolved in DMF and water, respectively, cast on the ZnSe crystal and dried by air-blowing; and phosphate buffer saline (PBS, pH=7.4) solutions in which hydrogels were immersed, were dropped on the crystal and dried by air-blowing. Due to the poor contacts between dried hydrogels and the ZnSe crystal, all the gels were wetted with PBS before IR scanning, and the spectra were processed with a background subtraction of the PBS solvents.

The IR spectra confirm the chemical composition of the hydrogels. The typical divided bands of symmetric —CH (CH$_3$)$_2$ group at 1388 and 1371 cm$^{-1}$ due to PNIPAAM were observed in the spectra of the hydrogels. The presence of the following peaks at 1759 (C=O stretching), 1211 (C—O—C asymmetric stretching), 1194 (O—CO stretching), 1110 (CH (CH$_3$)=O stretching) and 1050 (C—OCO stretching) cm$^{-1}$ in 90/10/00, 80/10/10, 80/15/05, and 70/20/10 gels suggested that PLLA had been successfully incorporated into the four hydrogels. It is worthy to mention that the intensities of all the above peaks were enhanced as the molar ratio of PLLA increased. Compared with PNIPAAM, the 90/00/10 gel showed a new peak at 1050 cm$^{-1}$. This new peak should come from dextran and could be due to a shifted band of C—OH stretching originally at ~1010 cm$^{-1}$ or C—OCO stretching, Scheme 1. Structure of NIPAAM-co-PLLA-co-dextran hydrogels.

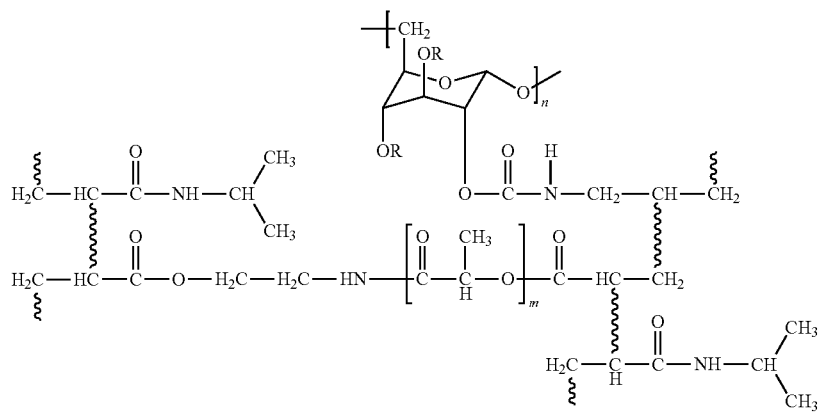

which is not clear at this stage. For the three-component 80/15/05 hydrogels, the characteristic bands of the dextran were either overlapped by the bands from the PNIPAAM and PLLA, or not observed due to small amount of the dextran. For the three-component 70/20/10 hydrogels, the peak at 1010 cm$^{-1}$ might be due the C—OH stretching of dextran component. The successful incorporation of PLLA and/or dextran into the copolymeric hydrogels was further confirmed by the following thermo-responsive and swelling property studies of the hydrogels.

1.1.6 Properties of Hydrogel NIPAAM-PLLA-DEXTRAN

The hydrogels comprised of NIPAAM, as a thermoresponsive unit, PLLA as a hydrolytically degradable and hydrophobic unit, and dextran as an enzymatically degradable and hydrophilic unit, combined both thermoresponsiveness and biodegradability in a single material. Weight measurements revealed that all the synthesized hydrogels with the molar feeding ratios of PLLA and dextran components between 0-30% and 0-20%, respectively, were thermo-responsive having a LCST at around 32° C. with volumetric phase change. The phase transition became less sharp as the molar feeding ratios of the NIPAAM component decreased and that of the PLLA component increased. The hydrogels containing PLLA component were hydrolytically degradable due to the hydrolytic cleavage of the PLLA ester bond into carboxylic acid, which was detected by the ATR-FTIR technique after the hydrogels were immersed in PBS (pH=7.4) at 25° C. for two months. The hydrogels containing PLLA component degraded more slowly at 37° C. above the LCST than at 25° C. below the LCST, which was confirmed by the combination of the ATR-FTIR and SEM techniques and weight loss measurements.

All the hydrogels swelled much more at 25° C. below the LCST than at 37° C. above the LCST, and their dynamic swelling profiles were significant different at these two temperatures. At 25° C. below the LCST, addition of 10 mol % dextran component into PNIPAAM had no effect on the swelling kinetics within 10 days, and all the other copolymeric hydrogels swelled less than the homopolymeric PNIPAAM hydrogels due to the high hydrophilicity of PNIPAAM polymer chains at 25° C. The more amount of hydrophobic PLLA component the hydrogels had, the less the hydrogels swelled.

At 37° C. above the LCST, due to the hydrophobicity of the PNIPAAM component, the hydrophilicity of the dextran component, and the degradation of the PLLA component, all the copolymeric hydrogels swelled more than the homopolymeric PNIPAAM hydrogels and showed sustained swelling for eight months. The dynamic swelling ratios of the hydrogels were strongly influenced by the combination of dextran and PLLA components. The three-component hydrogels, 80/10/10, 80/15/05 and 70/20/10, swelled significantly higher than the two-component hydrogels, 90/00/10 and 90/10/00, and their dynamic swelling ratios decreased with increasing the amount of the PLLA component within the first three months. After four months, the swelling ratios of 80/15/5 gels remained increasing at the highest rate and matched or exceeded 80/10/10 gels.

1.1.6.1 Thermoresponsive Properties.

Weighted hydrogel samples were immersed in PBS (pH=7.4) at 10° C. The temperature was raised every 24 h ranging from 10 to 60° C. Before each temperature adjustment, swollen gel samples were taken out from the solutions, carefully removed surface water by filter paper, and weighed. The swelling ratio q was defined as: $q=(W_t-W_0)/W_0$ (Eq. 1) in which $W_t$ and $W_0$ are the weights of the swollen and dry gels, respectively.

As illustrated in FIG. 1, the thermo-responsive study demonstrated that the swelling ratios of all the six hydrogels, PNIPAAM, 90/10/00, 90/00/10, 80/10/10, 80/15/05 and 70/20/10, decreased with increasing temperature when temperature was below 32° C., while remained relatively constant when temperature was above 32° C. Around 32° C., all the hydrogels had substantial volume collapse with turbid and white appearance. This 32° C. was defined as the lower critical solution temperature (LCST) of the hydrogels. As the molar ratio of NIPAAM decreased and that of PLLA increased, the phase transition of the hydrogels became less sharp. Both below and above the LCST, the six air-dried hydrogels demonstrated different swelling ratios, which were dependent on the copolymer compositions and the hydrophilic/hydrophobic balance. The effects of the copolymer compositions on the swelling ratios will be discussed in the next section.

1.1.6.2 Dynamic Swelling Properties.

Air-dried hydrogel samples were immersed in PBS (pH 7.4) at 25 and 37° C., respectively. Weights of the wet hydrogel samples were measured at different time points. Equation (1) was used to calculate the swelling ratio q.

Figure 2:
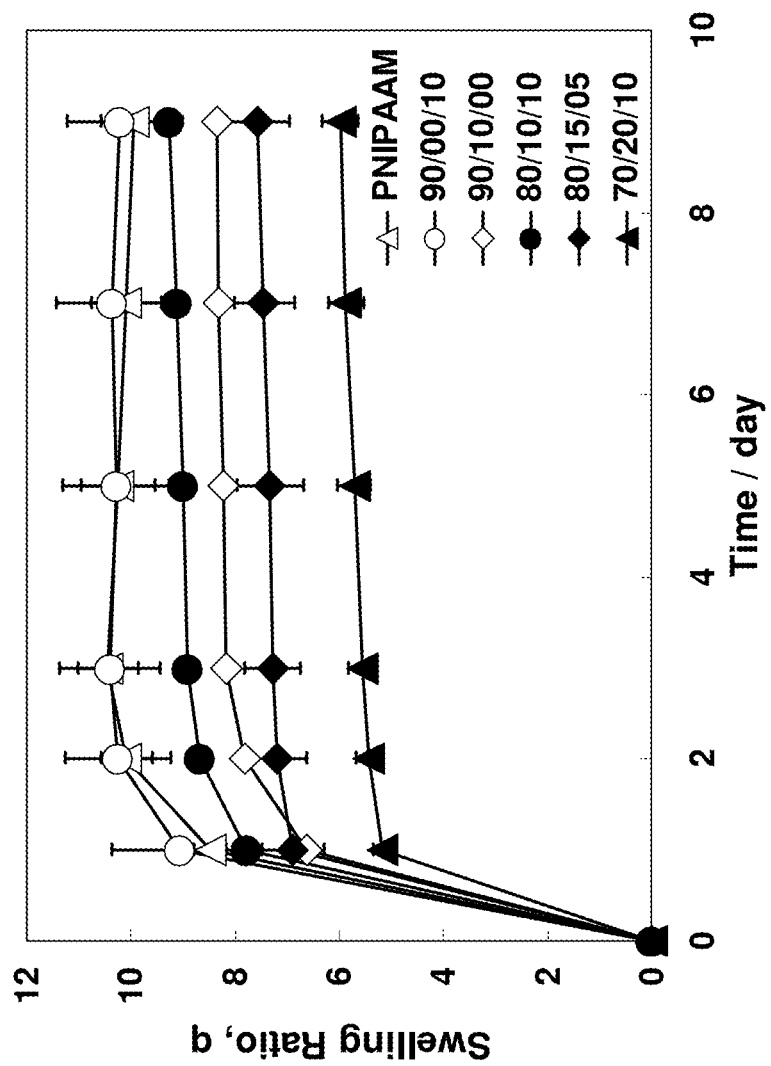
FIG. 2 is a chart showing the dynamic swelling profiles of a series of air-dried PNIPAAM-PLLA-Dextran hydrogels in accordance with one aspect of the present invention at 25° C. below the LCST in PBS (pH of about 7.4).

The dynamic swelling behaviors of the air-dried hydrogels were studied at temperatures both above and below the LCST. FIG. 2 illustrates the swelling profiles of the air-dried hydrogels as a function of time at 25° C. below the LCST. Because PNIPAAM is highly hydrophilic under this condition, all of the gels swelled rapidly at the beginning. Within less than 10 days, PNIPAAM and 90/00/10 gels, which have 100% hydrophilic compositions, reached their equilibrium swelling states. The incorporation of 10 mol % hydrophilic dextran segments (hydrogel 90/00/10) into PNIPAAM resulted in little change on the swelling behavior. Both PNIPAAM and 90/00/10 gels demonstrated slight "overshooting" during the swelling process at around three days, when the swelling ratios were temporarily above the equilibrium value. This overshooting might be attributed to a slower polymer chain relaxation than water diffusion. As the hydrophobic component PLLA was incorporated and increased, the overshooting swelling vanished. Also, the hydrogel swelling rates and ratios within the first 10 days decreased accordingly. A published study on hydrogels including both hydrophilic and hydrophobic components also illustrated that the swelling rate and ratio decreased with the increase of hydrophobic moiety. Comparing the two gels with equal amount of hydrophobic moiety, three-component 80/10/10 gels swelled moderately higher than two-component 90/10/00 gels, which might be attributed to a more heterogeneous structure. Interestingly, all the PLLA-included gels continued taking up water at fairly low rates without reaching equilibrium swelling for up to 2 months (data not shown). Although the extremely slow chain relaxation might play certain roles, this sluggish swelling was probably due to the gradual degradation of PLLA backbone, which generated pores inside the hydrogel network and consistently drew more water into it, as discussed in the following section of Degradation properties of hydrogels. It is also worthy to mention here that at 25° C., the PNIPAAM and 90/00/10 gels, which consisted of completely hydrophilic components, were weak in mechanical strength and difficult to handle. The mechanical property of the other four gels was apparently improved with the incorporation of hydrophobic PLLA component.

Figure 3:
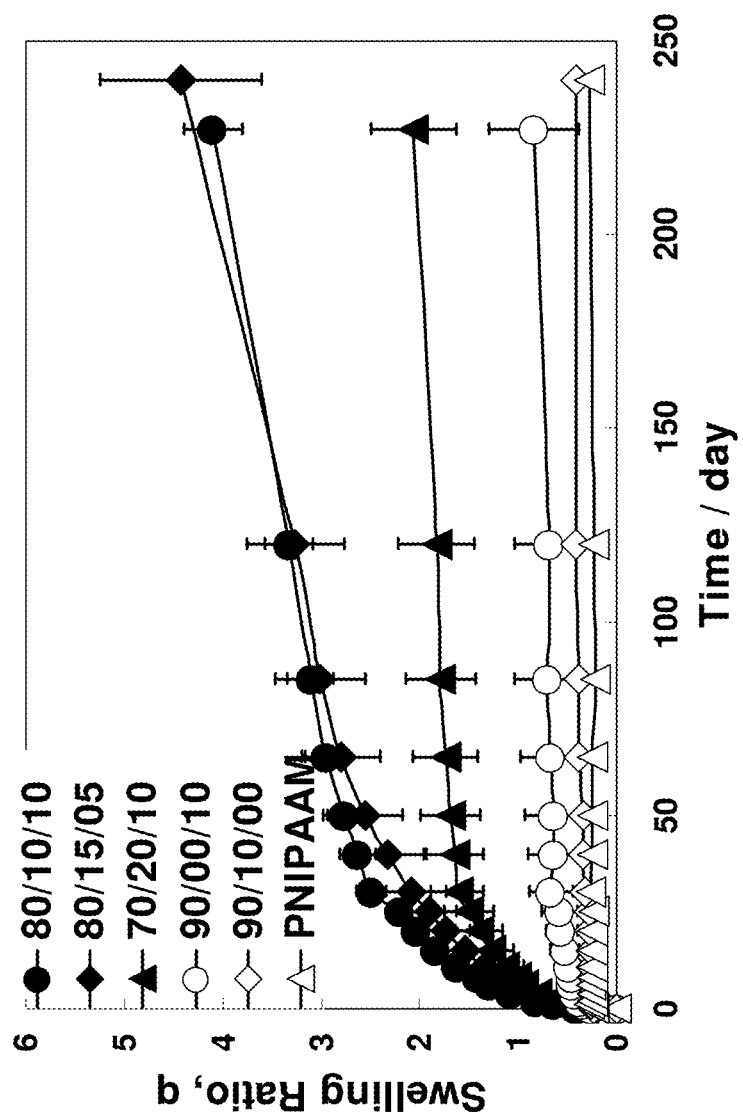
FIG. 3 is a chart showing the dynamic swelling profiles of a series of air-dried PNIPAAM-PLLA-Dextran hydrogels in accordance with one aspect of the present invention at 37° C., above the LCST, in PBS (pH of about 7.4).

At 37° C. above the LCST, the swelling profiles of the hydrogels were very different from those at 25° C. below the LCST. As shown in FIG. 3, all of the hydrogels swelled significantly less. At 37° C., PNIPAAM gels swelled only slightly and reached equilibrium state within a few hours due to well-known hydrophobicity above the LCST. After 10 mol % hydrophobic PLLA was incorporated with PNIPAAM, the 90/10/00 gels were supposed to have lower swelling ratios than or at least the same as the PNIPAAM gels had. Actually, the 90/10/00 gels maintained a subtly sustained swelling profile for up to approximately 50 days and reached an equilibrium swelling ratio only slightly higher than that of PNIPAAM gels. This may imply that the degradation of 90/10/0 gels was extremely limited under this condition due to high hydrophobicity of the gels. As 10 mol % hydrophilic dextran was incorporated with PNIPAAM, the 90/00/10 gels kept swelling at a fairly low rate after the initial fast swelling, and their swelling ratios were higher than those of the PNIPAAM gels. The reason might be due to the very slow degradation of urethane linkage of dextran component, which caused slow penetration of water from the surface to the center of the gels and corresponding slow relaxation of hydrophilic dextran chains. With the further incorporation of 10 mol % biodegradable PLLA component into the 90/00/10 gels, even though the hydrophilicity of the gels did not necessarily increase, the new 80/10/10 gels presented a consistently increasing swelling profile at a significantly higher rate for up to eight months. Although more heterogeneous polymers resulted from the incorporation of the third component PLLA might make certain contribution, the reasons for the higher swelling ratio and rate of the 80/10/10 gels relative to the 90/00/10 gels, might be largely attributed to the gradual degradation of the PLLA backbone which decreased the hydrophobicity of the polymer chains. For the same reason, the other two three-component gels, 80/15/05 and 70/20/10, also demonstrated sustained swelling profiles over an eight-month period. For all the three three-component gels, 80/10/10, 80/15/05 and 70/20/10, within the first three months, the swelling ratios and rates decreased with increasing the amount of PLLA moiety; while the swelling ratios of 80/15/5 gels remained increasing at the highest rate and matched or exceeded 80/10/10 gels at certain time after four months. It is well known that the solute permeability of hydrogels is influenced by the swelling ratio. Potentially used as controlled drug release devices, drug diffusion of the hydrogels studied in this paper may be regulated by adjusting hydrogel chemical composition, since the swelling behavior was strongly dependent on the composition, as also reported by others on copolymeric hydrogel studies.

1.1.6.3 Degradation Properties.

Degradation of the synthesized hydrogels are expected to be dependent on both environmental pH and the presence of dextranase due to the existence of PLLA and dextran segments, respectively. In this experiment, degradation study under normal physiological condition using PBS (pH 7.4) as the degradation medium is reported. Air-dried hydrogel samples were immersed in a small volume of PBS (pH 7.4) at 25 and 37° C., respectively. At selected time intervals, samples of the PBS solutions were taken and filtered through 0.45 μm Millipore membrane filters to remove any macroscopic pieces of gels fallen off from the hydrogels. The filtered solution samples were then studied by the ATR-FTIR technique to investigate the chemical composition changes due to the hydrolytic degradation of the hydrogels caused by the cleavage of ester bonds in PLLA backbones.

The morphology changes of hydrogels during the swelling at 37° C. was studied by SEM technique. Air-dried hydrogel samples were immersed in PBS at 37° C. At selected time intervals, one sample was removed from the solution, immediately frozen in liquid nitrogen, and lyophilized overnight, so that the swollen structure of the samples was retained. The dried samples were then coated with gold and observed under a JEOL JSM-6700F Field Emission SEM (Joel Ltd., Tokyo, Japan).

The air-dried hydrogel degradation study was conducted by using ATR-FUR technique, in which the air-dried hydrogel samples were incubated for about 2 months at 25° C. below the LCST. Since the solution samples were filtered through a 0.45 μm filter before the IR study, any macroscopic gel fragments that might have fallen apart from the hydrogel samples due to mechanical defect were excluded. Surprisingly, the PBS solutions for air-dried PNIPAAM gels showed typical peaks of PNIPAAM polymers, including amide I band at ~1670 $cm^{-1}$, amide II band at ~1540 $cm^{-1}$, and characteristic peaks of isopropyl group at 1388 and 1371 $cm^{-1}$. It was likely because that even though the PNIPAAM gels were thoroughly washed after syntheses (experimental section), there was a small portion of PNIPAAM chains physically entangled in the hydrogels. As the hydrogels swelled in the solution, polymer chains relaxed and the network structure became much looser, some of the entangled PNIPAAM chains diffused into the PBS solutions.

For all the air-dried hydrogels containing PLLA component, 70/20/10, 80/15/05 and 80/10/10, the IR spectra of their PBS solutions were similar to that of the PBS solutions of the PNPAAM gels at one month (data not shown): With time increasing to two months, an C=O stretching band at ~1720 $cm^{-1}$ were observed in all the hydrogels with PLLA component, suggesting the presence of carboxylic acid in the PBS solutions, and indicating the hydrolytic cleavage of the ester bonds of the PLLA backbone of the hydrogels. As the molar feeding ratios of the PLLA component increased, the intensity of the IR peak at 1720 $cm^{-1}$ also became higher. For the 70/20/10 gel with the highest amount of PLLA moiety, another two peaks were observed at 1600 and 1411 $cm^{-1}$. These two peaks were attributed to the C=O asymmetric and symmetric stretching of $COO^-$, which was formed by carboxylic acid in the saline buffer, respectively. As PLLA chains broke down, short PNIPAAM/dextran polymeric chains might also be freed from the hydrogel networks and enter the solutions. These short chains together with the diffused chains that were not covalently crosslinked in the hydrogels contributed to the other peaks in the IR spectra. Measurements of ATR-FTIR spectra for all of the hydrogels against their incubation times in PBS for up to two months were made. It was observed that the C=O stretching band at ~1760 $cm^{-1}$ of ester groups existed in all the hydrogels containing PLLA component over two month period (data not shown), indicating that degradation of PLLA had not completed within two months. Unfortunately, due to the heterogeneity and slow degradation of the hydrogels containing PLLA component, we could not obtain consistent IR spectra of the hydrogels at selected time intervals, so that we were not able to investigate the degradation of the hydrogels by following the intensity changes of the C=O stretching band at ~1760 $cm^{-1}$ of the ester groups of the hydrogels as a function of time.

On the other hand, at 37° C. above the LCST, for up to 3 months the degradation of all the hydrogels was not able to be detected in either PBS solutions or hydrogel forms by the above ATR-FTIR methods. All the PBS buffer solutions for gel incubation showed no trace of chemicals. This can be explained that all the hydrogels were relatively hydrophobic at 37° C. They remained dense structures in the buffer solutions due to the low swelling ratios, so that water molecules could not have sufficient access to the PLLA backbone and effectively break the ester bonds to generate enough signals for the ATR-FTIR detections. However, the following weight loss measurements and SEM results demonstrated that the hydrogels containing PLLA component indeed degraded at 37° C.

Figure 4:
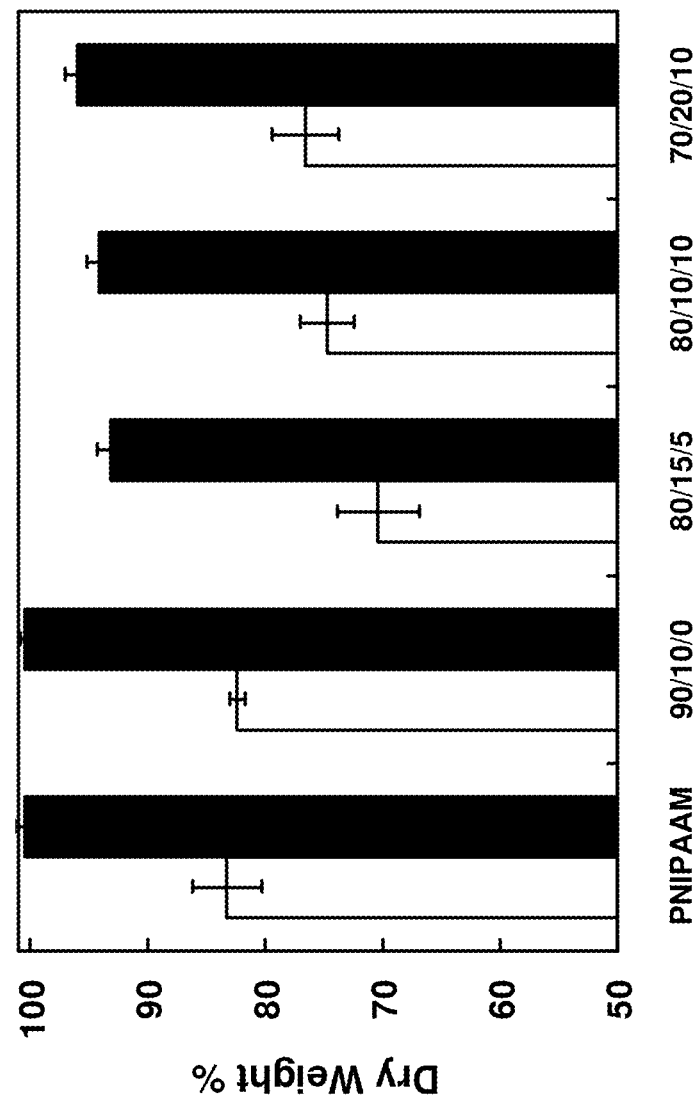
FIG. 4 is a bar graph showing weight percentage of dry hydrogels in accordance with an embodiment of the present invention after nine-months of incubation in PBS (pH of about 7.4) at 25° C. (white bars) and 37° C. (black bars).

After approximately nine months of incubation, hydrogels were removed from the PBS, washed with water for two days, and re-dried in the air for several days until no further weight loss. The dry weights of the hydrogels were measured and compared with the initial values. FIG. 4 shows weight percentage of dry hydrogels after nine months of incubation in PBS (pH of About 7.4) at 25° C. (white bars) and 37° C. (black bars).

At 25° C., all the hydrogels lost noticeable amounts of weight. As discussed earlier, the weight loss of PNIPAAM gels, which were supposed to be non-degradable, might be attributed to the diffusion of physically entangled polymer chains from the loose network under this condition over time. According to the IR spectra, it is reasonable to propose that the weight loss of the PLLA-incorporated gels were due to, or partially due to degradation. The weight loss amount was related with the compositions of the hydrogels, with 80/15/05 gels having the highest level. The incorporation of dextran may have benefited the degradation, as all the three-component gels lost more weights than the 90/10/0 gels. There might be an optimal ratio between hydrophobic PLLA and hydrophilic dextran segments that could lead to a desired weight loss degree, as more PLLA would bring additional hydrolysable units to the gels, but meanwhile decreasing the hydrophilicity of the network and water accessibility to the polymer chains.

On the other hand, the weight loss at 37° C. was much less dramatic. As expected, PNIPAAM gels did not lose weight due to the non-degradability. Because of the high hydrophobicity and dense polymer network structure, the weight loss due to entangled chain diffusion which was likely to occur at 25° C. did not happen. 90/10/00 gels did not show any significant weight loss as well, which could be attributed to the hydrophobicity of the polymer network and the difficulty of water access to polymer chains to hydrolyze PLLA backbones. Similarly to 25° C., all the three-component gels lost certain amounts of weight, which was dependent on the chemical compositions; and again, the importance of incorporating hydrophilic dextran segment into the hydrogels to enhance degradation was apparent.

Surface morphologies of the hydrogels, PNIPAAM, 90/10/00 and 80/15/05, after incubation in PBS (pH of About 7.4) at 37° C. for 10 h, and 4 and 40 days were measured by SEM. From the kinetic swelling results we have known that an initial fast swelling existed for all the hydrogel samples due to the rapid water diffusion and hydrogel surface hydration. It can be seen from the SEM pictures at 10 h, all the samples presented surface morphology with big open pores of size 5-10 μm. Because of the homogenous nature of PNIPAAM gel, the pores of PNIPAAM gel were in more regular shape and size compared with those of the other two gels 90/10/00 and 80/15/05, which were relatively more heterogeneous. Interestingly, at 4 days, all the three hydrogels demonstrated a basically flat surface with numerous small pores. This might be because that after the fast hydration within the early several hours, the polymer chains continuously relaxed and rearranged themselves. In accordance with the swelling results, at 4 days, the 80/15/05 gels had higher swelling ratios than the 90/10/00 and PNIPAAM gels had, and their average pore size was also larger than those of the later two gels. The polymer chain rearrangement of a hydrogel would stop at certain point when the hydrogel stops swelling and reaches balanced structure; while the chain relaxation would continue as the hydrogel keeps swelling. From 4 to 40 days, the surface morphology of PNIPAAM gel remained approximately the same since it already reached equilibrium swelling state within the first 4 days. On the other hand, the 90/10/00 and 80/15/05 gels were in different situations. The 90/10/00 gel remained a rather low swelling rate during this period; therefore, bigger pore sizes were seen at 40 days than at 4 days (data not shown). As discussed briefly in the previous section, an extremely slow PLLA backbone degradation might also play certain role in this continuous swelling and pore size increase. The 80/15/05 gel kept swelling at a much higher rate due to the incorporation of hydrophilic dextran and the PLLA degradation, hence resulted in even larger pores and some fractural structures.

1.1.7 Hydrogels as Drug Release Vehicles 1.1.7.1 In Vitro NGF Release Study

Hydrogel samples (3/1 mm/mm in diameter/thickness) were immersed in a concentrated nerve growth factor (NGF, Roche Diagnostics Corp., Indianapolis, Ind., 25 mg·ml$^{-1}$) in PBS (pH 7.4, containing 1 w/v % bovine serum albumin (BSA)) solution at 10° C. for at least 24 hours to equilibrate. After loading, the samples were immediately freeze-dried. Release experiments were carried out by incubating each NGF-loaded dry gel sample in 2.5 ml PBS (pH 7.4, containing 1 w/v % BSA) at 37° C. At selected time points, 1 ml of release solution was taken for NGF concentration analysis by enzyme-linked immunosorbent assay (ELISA); 1 ml of fresh PBS (pH 7.4, containing 1 w/v % BSA) was replaced. Representative release experimental data are shown in Table 2. All the gels showed an initial burst release within the first two days followed by a low-rate sustained release for up to 15 days. The NGF release amount increased in the order of PNIPAAM gel>90/00/10 gel>70/20/10 gel>80/15/05 gel>80/10/10 gel. The three-component hydrogels 70/20/10, 80/15/05 and 80/10/10 showed more obvious increased NGF release with time, than the other hydrogels PNIPAAM and 90/00/10 without PLLA, indicating that PLLA played an important role for sustained NGF release. The results demonstrated that NGF release strongly depended on the properties of each hydrogel, including swelling behavior, hydrophilic/hydrophobic balance, biodegradation and NGF/polymer interaction.

TABLE 2

| Cumulative NGF released in PBS (pH = 7.4) at 37° C. normalized by dry sample weight (ng NGF/mg dry gel)* | | | |
|---|---|---|---|
| Hydrogel | 1 day | 5 day | 15 day |
| PNIPAAM | 96 ± 20 | 111 ± 29 | 117 ± 33 |
| 90/00/10 | 108 ± 22 | 151 ± 33 | 159 ± 36 |
| 70/20/10 | 247 ± 27 | 278 ± 70 | 307 ± 84 |
| 80/15/05 | 363 ± 97 | 524 ± 149 | 549 ± 143 |
| 80/10/10 | 355 ± 83 | 594 ± 83 | 638 ± 86 |

*Standard deviations are based on four experiments

The hydrogels showed thermoresponsive properties and the LCST was around 32° C., typical to that of PNIPAAM. The hydrogels were also hydrolytically biodegradable with pore sizes increasing after about 4 months. The swelling behaviors of the hydrogels were different at temperature above (37° C.) and below (25° C.) the LCST and strongly depended on the hydrophilicity and hydrophobicity of the copolymers. The release profiles of NGF from the hydrogels were also different at temperatures above (37° C.) and below (25° C.) the LCST, depending on the swelling of the hydrogels and the interaction between the NGF and the hydrogels. In conclusion, the hydrogels have great potentials in controlled and sustained release of the NGF through changing their copolymer compositions, and thermo-responsive and biodegradable properties.

1.1.7.2 Cellular Toxicity Study.

Hydrogel samples used in cellular toxicity study were sterilized in 70% ethanol for several hours and equilibrated in cell culture medium for one day. PC-12 cells were seeded onto 24-well plates at a density of ~75,000 cells/well (500 μl/well) in RPMI 1640 medium containing 5% fetal bovine serum, 10% heat-inactivated horse serum, 3.6 mM L-glutamine, and 1% penicillin/streptomycin, and incubated in a humidified incubator under a 5% $CO_2$ atmosphere at 37° C. for 24 hours. Sterilized hydrogels were then placed into the wells to incubate together with the cells. Cell viability was studied using MTT assay for one day and six days after hydrogels were added. For six-day's study, medium was changed partially at the third day. For all cases, the average cell viability was between 85-100%, indicating the hydrogels were not toxic to PC-12 cells.

1.1.7.3 Evaluation of Biological Activities of NGF Released from the Hydrogels.

Same cell culture and gel placement procedures were follows as for the toxicity study, except that NGF-loaded dry gels were used, and that ~20,000 cells were seeded in each well at the beginning. 1, 2 and 5 days after the addition of hydrogels samples, cell differentiation and neurite extension were observed under an inverted optical microscope (Nikon ECLIPSE TE2000-5) and images were captured by a digital camera. For all the hydrogel samples, small short neurites appeared on a number of cells after one day culture, and the number of the cells with neuritis and the length of neurites increased with culturing time (data not shown). Cells cultured without hydrogel samples were used as negative controls, and showed no noticeable neurite outgrowth. The results suggested that NGF released from the designed hydrogel was biologically active and promoted neurite outgrowth.

1.2 Synthesis of Hydrogel NIPAAm-Dextran Derivative

In this experiment, a new bioresponsive-co-biodegradable hydrogel system was prepared incorporating NIPAAm and dextran derivative macromer, dextran-(2-hydroxyethyl-methacrylate)-lactate.

1.2.1 Materials:

Dextran=15,000-20,000) was purchased from Polysciences, Inc., Warrington, Pa. NIPAAm, 2-hydroxyl-methacrylate (HEMA), 4-(N,N-diethylamino)pyridine (DMAP), N,N'-carbonyl-diimidazole (CDI), L-lactide, stannous octoate, tetrahydrofuran (THF), dimethyl sulfoxide (DMSO), N,N,N'N'-tetramethylethylenediamine (TEMED), potassium peroxydisulfate (KPS), BSA, and Bradford reagent were obtained from Sigma-Aldrich, Inc., St. Louis, Mo. Methylene blue was obtained from Acros, Inc., New Jersey. All the chemicals were used as received.

1.2.2 Synthesis of Dextran-lactateHEMA Macromers.

Dextran-(2-hydroxyethylmethacrylate)-lactate (Dex-lactateHEMA) macromer was synthesized according to a published method (Wolthuis, et al. Polymer, 1997, 38, 6235-6242). For example, L-lactide and 2-hydroxyethyl methacrylate (HEMA) with 1:1 molar ratio were first reacted at 110° C. for one hour in the presence of catalyst $SnOct_2$ to obtain HEMA-lactate. Secondly, N,N'-carbonyldiimidazole (CDI) was reacted with the above HEMA-lactate product at 1:1 feeding molar ratio at room temperature in THF for 16 h to obtain HEMA-lactateCl. Finally, a calculated amount of dextran was reacted with HEMA-lactateCI (HEMAlactateCI: glucopyranose=7:1 molar ratio) in the presence of catalyst 4-(N,N-dimethylamino) pyridine (DMAP) in dimethyl sulfoxide (DMSO) at room temperature for four days to obtain the Dex-lactateHEMA macromer. The average length of lactate spacer ($DP_{av}$) is equal to 3, and degree of substitute (DS; amount of methacrylate groups per 100 dextran glucopyranose residues) is equal to 4.6.

1.2.3 Synthesis of Hydrogel NIPAAm-Dextran Derivative.

Total amount of 450 mg NIPAAm and Dex-lactateHEMA at different weight ratios (7:2, 6:3, 5:4, 4:5) was dissolved in 2.28 ml phosphate buffer saline (PBS, pH=7.4) solutions under nitrogen. After dissolution, 270 μL KPS in PBS solution (conc. 50 mg/ml) was added and mixed well. Thereafter, 75 μL 20% (v/v) TEMED in PBS was added. The mixture was mixed thoroughly and quickly injected in between two glass plates separated by Teflon® spacer (thickness 1.6 mm) and the gelation was allowed to proceed at room temperature for one hour. Disc-shaped gel samples (about 8 mm in diameter) were then cut off and washed in large volume of 50 vol % ethanol/water solvents for 30 minutes and dried in the air till no further weight loss.

Figure 5:
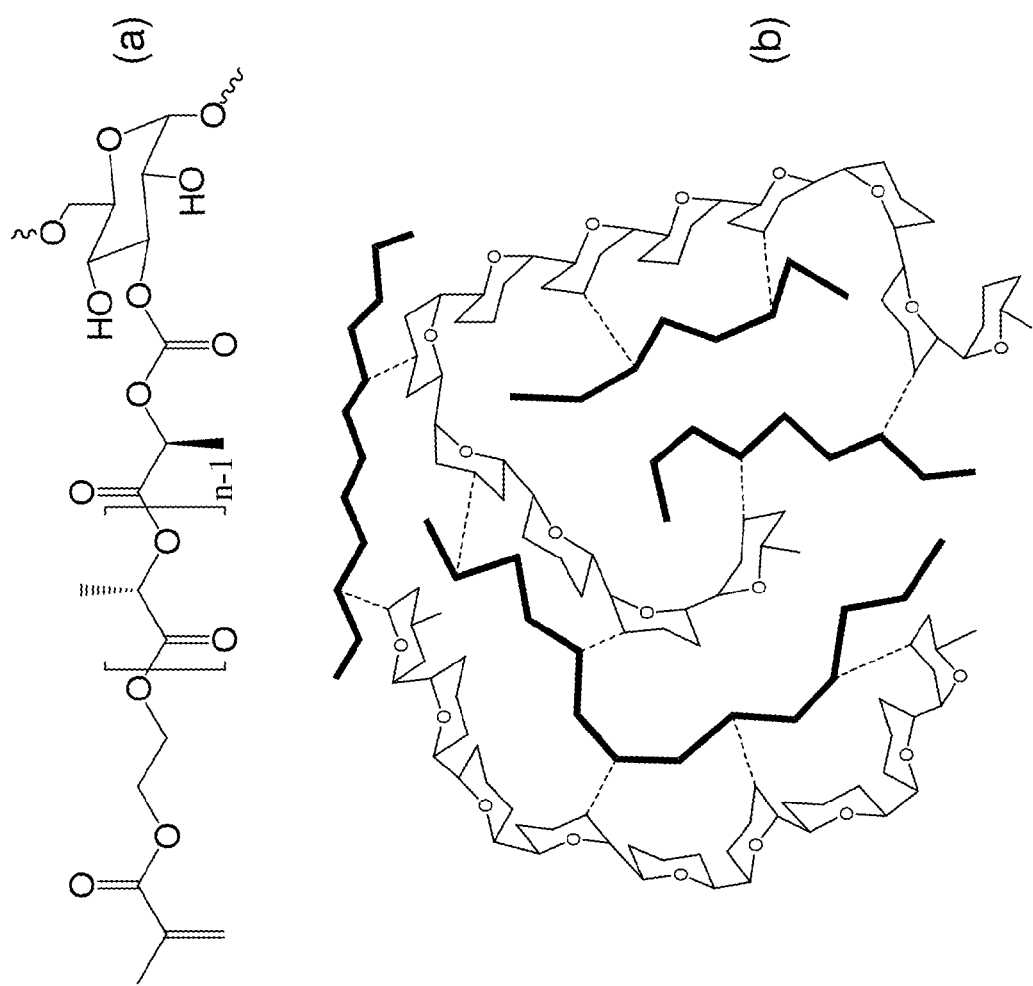
FIG. 5 is a schematic chemical structure of Dex-lactate-HEMA (a) and NIPAAm-co-Dex-lactateHEMA hydrogels (b) in accordance with an embodiment of the present invention.

The chemical structures of Dex-lactateHEMA macromer and NIPAAm-co-Dex-lactateHEMA hydrogels are sketched in FIG. 5. Hydrogels synthesized with initial NIPAAm/Dex-lactateHEMA feeding ratios (w/w) of 7:2, 6:3, 5:4, and 4:5 were denoted as gels 7/2, 6/3, 5/4, and 4/5, respectively. The synthesized gels were flexible and rubbery. The gels with the highest NIPAAm composition were basically transparent. With the increase of dextran component, the heterogeneity of the gels increased, samples with higher dextran composition became semi-transparent.

1.2.4 Properties of Hydrogel NIPAAm-Dextran Derivative

1.2.4.1 Thermoresponsive properties.

Weighted hydrogel samples were immersed in PBS (pH=7.4) at 10° C. The temperature was raised every one hour, ranging from 10 to 60° C. Before each temperature adjustment, swollen gel samples were taken out from the solutions, carefully removed surface water by filter paper and weighed. The swelling ratio q was defined as: $q=(W_t-W_0)/W_0$ (Eq. 1), in which $W_t$ and $W_0$ are the weights of the swollen and dry gels, respectively.

Figure 6:
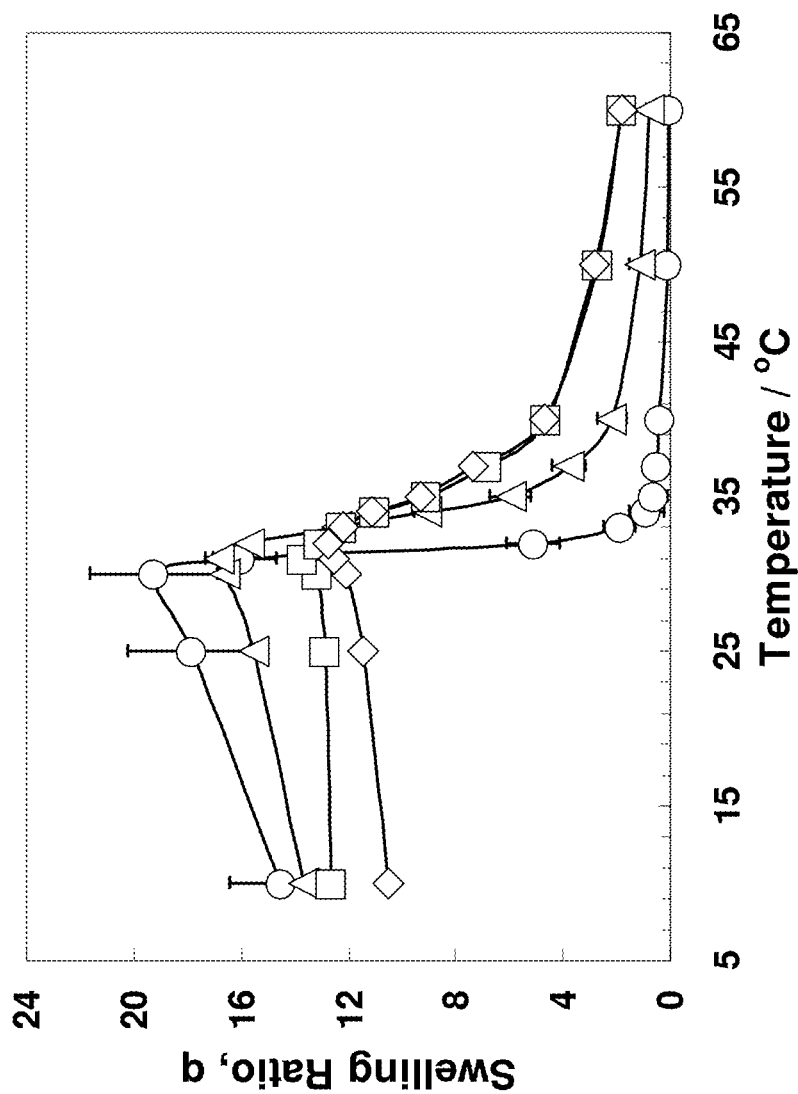
FIG. 6 is a chart showing the swelling ratios for a series of NIPAAm-co-Dex-lactateHEMA hydrogels in accordance with one aspect of the present invention. In particular, the chart shows thermoresponsive properties of the hydrogels by measuring swelling ratios as a function of temperature from 10 to 60° C. after equilibrium for 1 hour at each temperature interval in PBS solvent (pH of about 7.4).

All the hydrogel showed a sharp volume phase transition at slightly higher than 32° C. (FIG. 6), which is the typical LCST of NIPAAm-based polymer. With the increase of Dex-lactateHEMA, the transition point was shifted slightly to higher temperature. In this study, despite the incorporation of short hydrophobic oligolactate spacer, the Dex-lactateHEMA macromer was still hydrophilic, which explained the slight increase of LCST.

It was observed in this system that when the thermoresponsive NIPAAm moiety decreased, the phase transition of the hydrogel became less sharp, which indicated a decrease in temperature sensitivity. Interestingly, at a temperature below the LCST, swelling ratios of the hydrogels somewhat increased with the temperature, which was not typical for thermoresponsive gels. This could be possibly because that rapid degradation of this system resulted in breaking some of the effective crosslinks and favoring more water uptake. However, when temperature reached the LCST, strong hydrophobic interaction of the polymer chains dominated, even though degradation might proceed over time, significant amount of water was dispelled from the hydrogel. Phase separation and a substantial decrease of swelling ratio were also observed at the LCST.

1.2.4.2 Degradation Properties.

Dry hydrogel samples were immersed in PBS (pH of About 7.4) at 25 and 37° C., respectively. At different points in time, samples were removed from the solvents and dried in air overnight. Weight of the dried gels were measured before the samples were placed back to PBS for continuous degradation. PBS solvents were replaced frequently.

Figure 7:
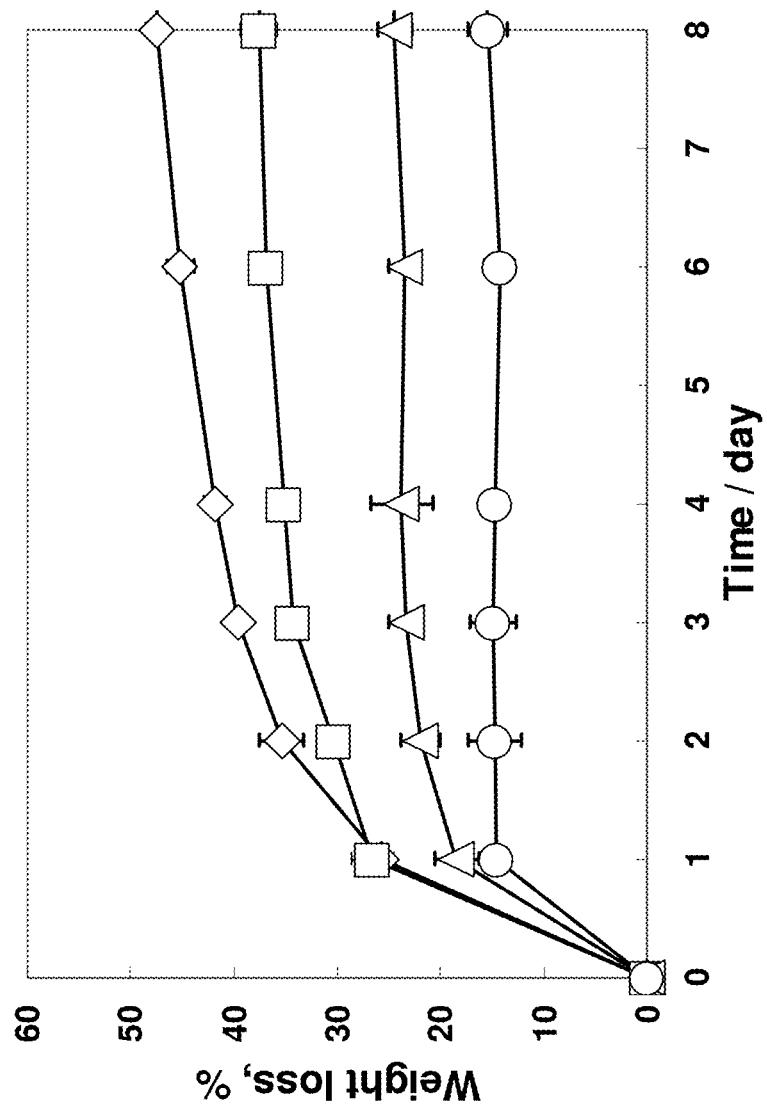
FIG. 7 shows weight loss of NIPAAm-co-Dex-lactate-HEMA hydrogels 7/2 (○), 6/3 (△), 5/4 (□), and 4/5 (◇) in accordance with one aspect of the present invention in PBS (pH of about 7.4) at 37° C.

The hydrogels degraded fast at temperatures lower than the LCST (FIG. 7). At 25° C., the samples started to disintegrate in PBS (pH of About 7.4) after one, two, four, and five days for 7/2, 6/3, 5/4, and 4/5 gel, respectively, and gradually dissolved afterwards. As the results presented in previous section show, all the hydrogels were highly hydrophilic and swollen at temperatures below the LCST; therefore, abundant water could easily access and hydrolyze the ester bond's of oligolactate units, thereafter break down the crosslinking. It is understandable that hydrogels with higher Dex-lactate-HEMA composition possessed more crosslinks and ester bonds, and needed longer time to degrade.

In contrast, at 37° C., above the LCST, the degradation was much slower. FIG. 7 presents the weight loss results of the hydrogels under such condition. The rates of the weight loss of all the hydrogels were high within the first two days and decreased with time afterwards. This could be explained as follows. As the crosslinks broke, the freed hydrophilic dextran segments easily diffused into the aqueous environment. Some PNIPAAm segments also became free; however, their release into the medium was much slower and more difficult due to the hydrophobic interaction, especially the segments with relatively high chain length. This part of PNIPAAM segments might entangle with each other and with the hydrogel network as well, which increased the hydrophobicity of the remaining gel. As a result, water diffusion and access to the polymer chains became limited and obstructed, leading to a reduced degradation speed. Moreover, the degradation rate of the hydrogels strongly depended on the hydrogel composition. As shown in FIG. 7, the degradation rate decreased with the increase of NIPAAM amount, and became extremely slow after two days for 7/2 and 6/3 gels owning to the increasing hydrophobicity of the gels. Research groups grafted dextran to a copolymeric chain of NIPAAm and N,N-dimethylacrylamide (DMAAm) and synthesized hydrogels from the copolymer. (Biomacromolecules, 2001, 2, 874-879; Macromol Chem. Physic, 1998, 199, 2613-2618.) They studied the degradation behavior of the hydrogels under the function of dextranase at different temperatures. Their results suggested that enzymatic degradation of the hydrogels was faster at temperature above the LCST than below, which was opposite to our discovery on the hydrolytic degradation, possibly due to the different mechanism of enzymatic and hydrolytic degradations. Since our hydrogels would also be susceptible to enzymatic degradation, the manipulation of degradation may be even more flexible.

1.2.4.3 Hydrogel Dynamic Swelling Properties.

Dry hydrogel samples were immersed in PBS (pH 7.4) at 37° C. Weights of the wet hydrogel samples were measured at different time points. Equation (1) above was used to calculate the swelling ratio q. PBS solvents were replaced frequently.

Figure 8:
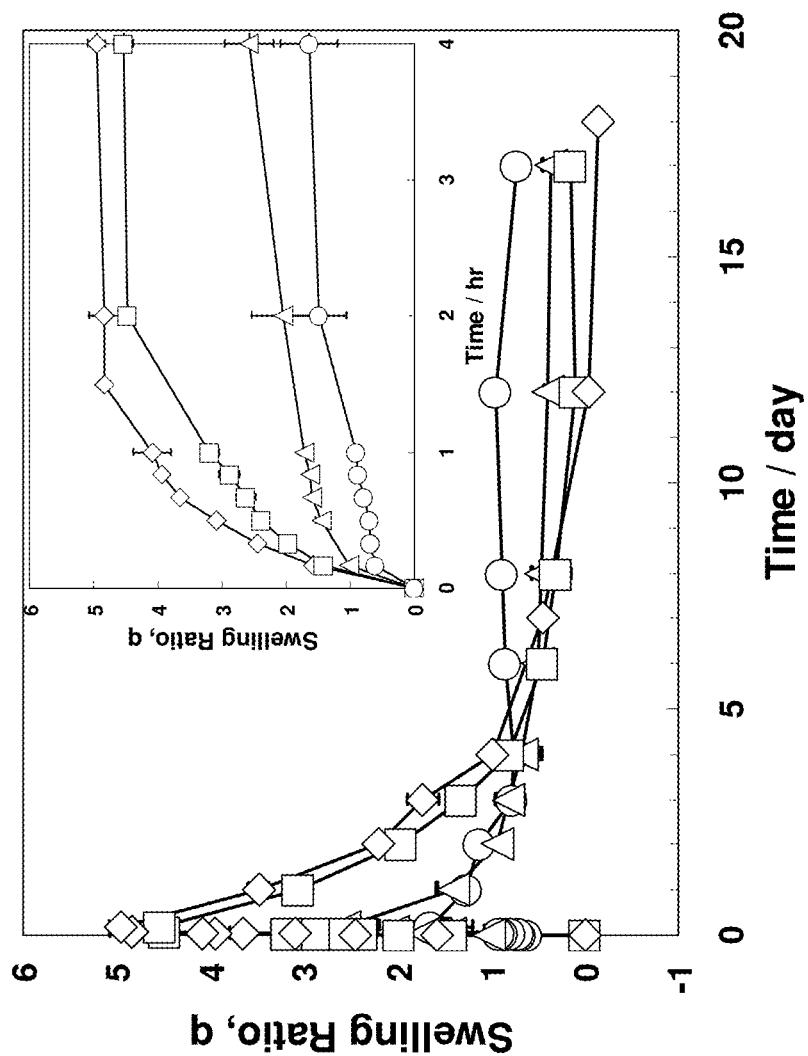
FIG. 8 shows swelling profiles of NIPAAm-co-Dex-lactateHEMA hydrogels 7/2 (○), 6/3 (△), 5/4 (□), and 4/5 (◇) in accordance with one aspect of the present invention in PBS (pH of about 7.4) at 37° C. The insert shows swelling data in the first few hours.

Swelling profiles of the hydrogels in 37° C. PBS (pH 7.4) are depicted in FIG. 8, with the insert showing the swelling at early hours. The swelling ratios of all the hydrogels increased quickly at the beginning, due to fast water diffusion. A burst of swelling for hydrogels composed of dextran and PLA was attributed to the strong interactions between water and the hydrophilic dextran. An additional contribution to the burst swelling was attributed to the breakdown of crosslinks leading to a loosened network structure favorable for water diffusion. As mentioned in the previous section, with the degradation proceeding, freed hydrophilic dextran segments quickly dissolved in the surrounding medium, not only causing decrease in hydrogel mass, but also leaving behind a hydrogel network becoming more and more hydrophobic. As a result, water was expelled from the gels. The reduced water and hydrogel mass both contributed to the decrease of swelling ratios after reaching a maximum within a few hours. It is easy to understand that hydrogels with higher Dex-lactate-HEMA moiety had a faster initial swelling and reached a higher maximum swelling ratio. As presented in the previous section, the mass loss rate of the hydrogels decreased with time, when the mass loss entered the slow stage, change in hydrogel hydrophilicity also became less dramatic, resulting in swelling ratios decrease at a lower rate, especially for the hydrogels with higher NIPAAm moiety. For example, swelling ratios of 7/2 and 6/3 gels reached a rather stable stage with little future decrease after 4 days while 5/4 and 4/5 gels remained a slowly reducing trend within 18 days of the study period.

1.2.5 In vitro Release of Drugs.

To test the potential of the developed hydrogels as drug release devices, two model drugs (22.5 mg) were loaded during the hydrogel synthesis, which were methylene blue and bovine serum albumin (BSA), representing small molecules and protein drugs, respectively. BSA- or methylene blue-loaded dry gels were immersed in a certain volume of PBS (pH 7.4) at 25 or 37° C. At selected time points, small volume of samples were taken and tested for solute concentration. The same volume of fresh PBS (pH 7.4) was replaced to maintain a constant volume of release medium. Concentration of methylene blue was measured by a UV spectrophotometer at 668 nm. Concentration of BSA was determined through Bradford protein assay.

Figure 9:
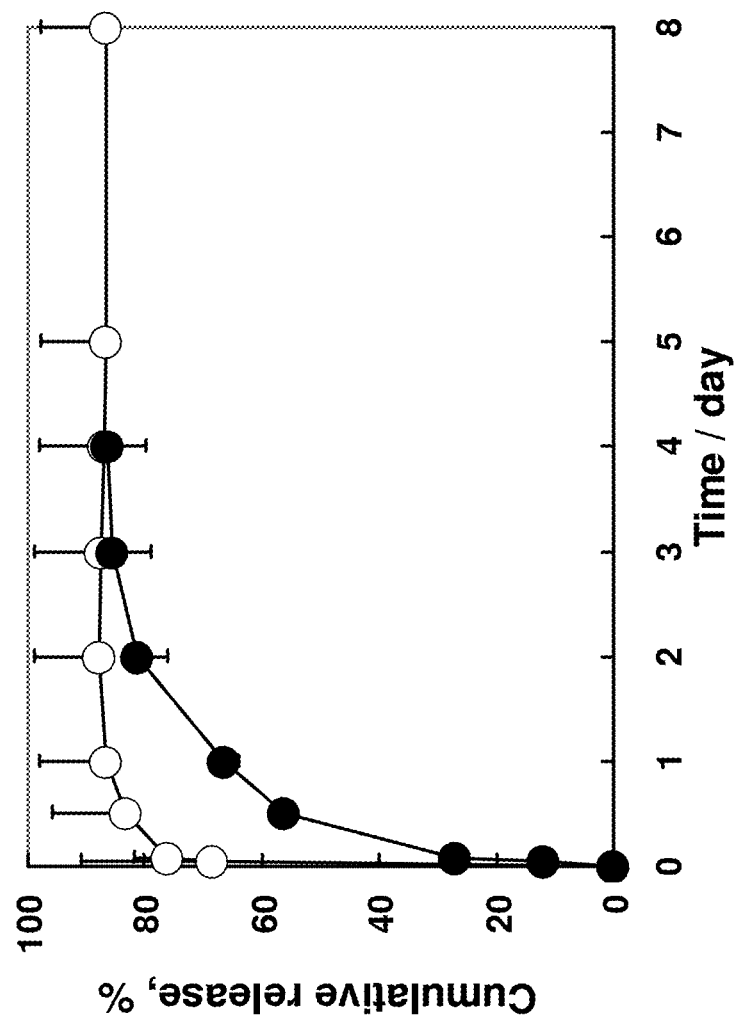
FIG. 9 shows the release rate of methylene blue from a NIPAAm-co-Dex-lactateHEMA gel 5/4 in accordance with one aspect of the present invention in PBS (pH of about 7.4) at 25 (●) and 37° C. (○).

In vitro release profiles of methylene blue at 25 and 37° C. are depicted in FIG. 9. At 25° C., data were collected before the hydrogels started disintegrating. Interestingly, release rate was higher at 37 than at 25° C., suggesting that the release was not controlled by either swelling or degradation. At 37° C., the release profile was characterized by an extremely high initial burst effect that released more than 70% loaded drugs. The burst effect is common in hydrogels as well as other drug delivery devices and can be caused by different reasons. In our systems it is likely the fast water diffusion and network hydration caused the initial rapid release of the drug. Considering that methylene blue has low molecular weight of 320, its diffusion into the release medium was hardly hindered by the hydrogel network. The degradation of the hydrogel might also play certain role in freeing drug molecules, but it may not be dominant. The drug release reached a stable stage after three days. A small portion of the drug was trapped inside the hydrogel and might be released slowly as the hydrogel degraded in a long term of view. It was not expected to find that release of methylene blue at 25° C., below the LCST, was slower. This could be addressed as follows. At 25° C., the hydrogels were highly hydrophilic and swollen. During degradation and before the networks disintegrated, they kept swelling due to the decreased crosslinks and loosened structure. This continuous swelling of the gels decreased the drug concentration gradient across the gel and the gel/medium interface, therefore, release rate was reduced.

Figure 10:
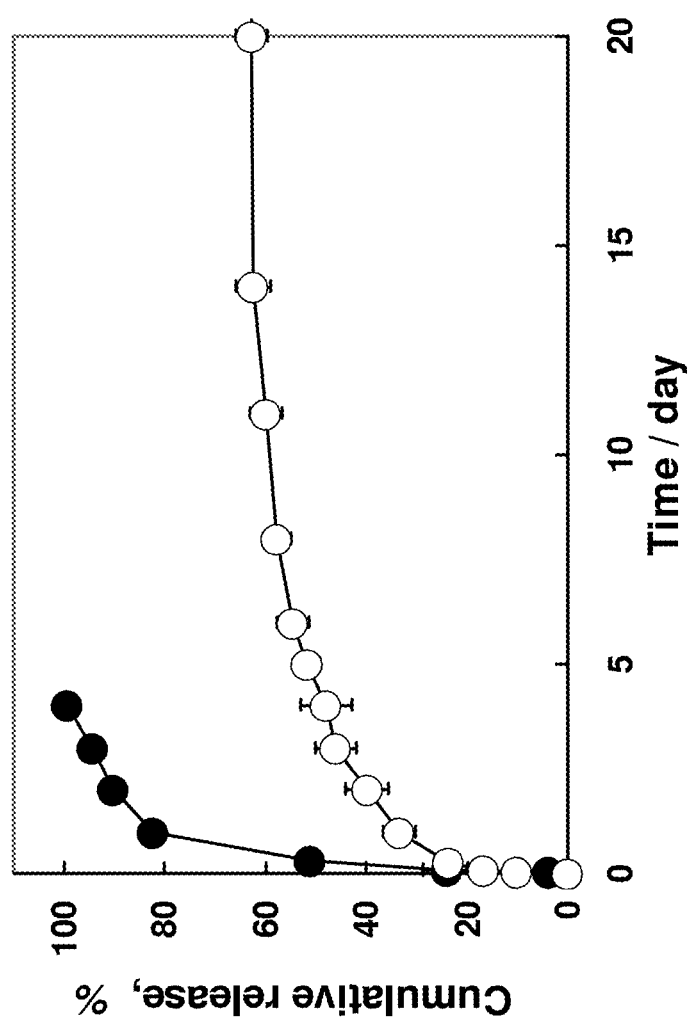
FIG. 10 shows the release rate of BSA from a NIPAAm-co-Dex-lactateHEMA gel 5/4 in accordance with one aspect of the present invention in PBS (pH of about 7.4) at 25 (●) and 37° C. (○).

The release profiles of model protein BSA are demonstrated in FIG. 10. At 25° C., data were collected before the hydrogels started disintegrating. At temperature below the LCST, 25° C., BSA was continuously and quickly released out form the hydrogels with completion at 4 days. This release trend of BSA was similar to that of smaller molar mass methylene blue. The results suggested that due to the highly swollen hydrogel and loosened polymer network structure at the temperature below the LCST, molecular size of the drugs showed little influence on their release profiles. In another word, drug molecules were much smaller than the mesh space of the polymer network. At 37° C., above the LCST. BSA release curve was featured by a moderate initial burst followed by a sustained release of diminishing rate for up to at least 20 days. These results could be explained as follows. At 37° C., the hydrogel network structure was relatively dense due to its hydrophobicity. In this case, drug diffusion was hindered and the release was mainly controlled by degradation, as the BSA release followed a similar trend of 5/4 gel degradation (see FIG. 7). Up to 20 days, around 40% of the loading BSA was retained inside the hydrogel. With the slow degradation proceeding, more drug might be released out at a low rate.

From this study, it was concluded that drugs of different molecular weights can be loaded in the hydrogels and released at different temperatures. Release of small molecular solute methylene blue was diffusion-controlled and slower at 25° C. than at 37° C. due to the higher hydrophilicity of the hydrogels and reduced concentration gradient at 25° C. than at 37° C. Release of protein BSA was diffusion-controlled at 25° C. and degradation-controlled at 37° C. As shown by this experiment, these hydrogels combined the advantages of both thermoresponsive and biodegradable polymers.

2.0 Dendrimers 2.1 Dendrimer Synthesis.

Figure 11:
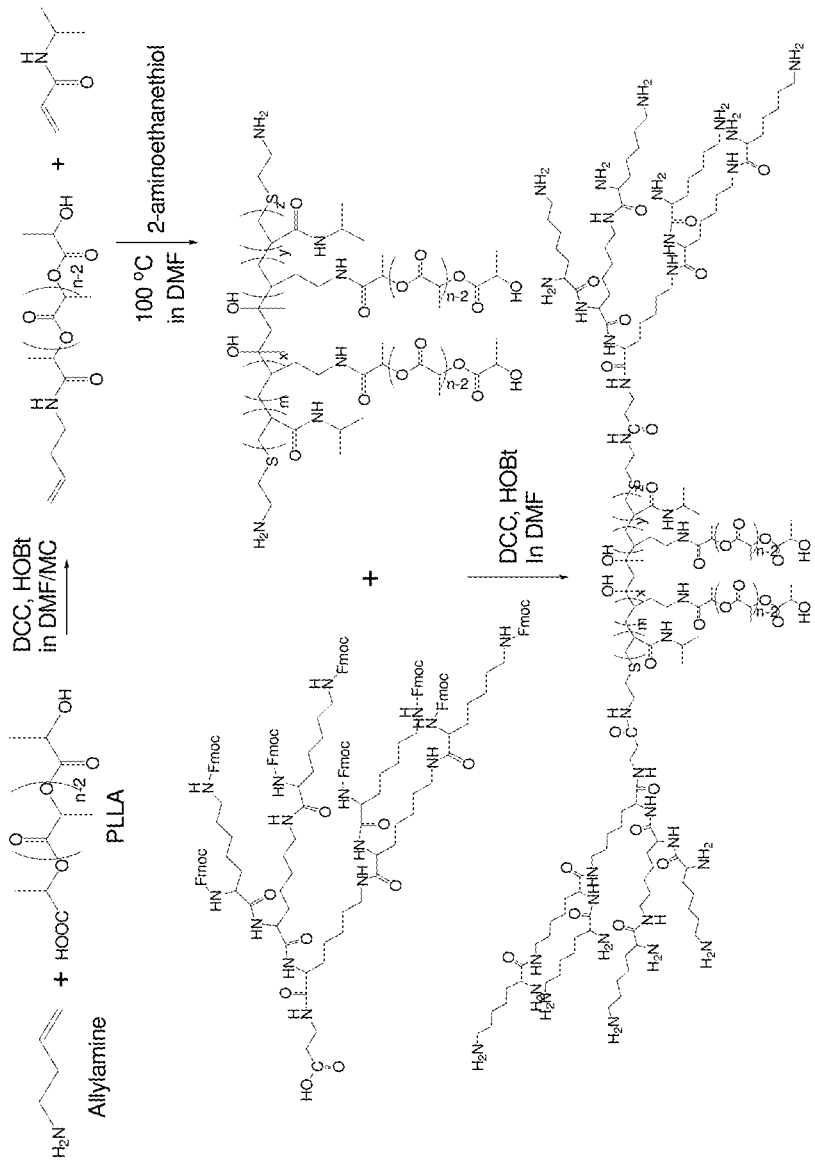
FIG. 11 shows a synthetic scheme for preparing dendrimers in accordance with one aspect of the present invention.

The dendrimers were synthesized by conjugating poly(L-lysine) (PLL) dendron with PNIPAAM grafted with PLLA. PNIPAAM grafted with PLLA was synthesized by free radical polymerization (FIG. 11).

2.1.1 Synthesis of Allyl-PLLA.

Poly(L-lactic acid) (PLLA, $M_w$=2000 g mol$^{-1}$, Polysciences, Inc., Warrington, Pa.) terminated with allyl groups was synthesized by 1,3-dicyclohexylcarbodiimide (DCC, Aldrich) coupling reaction of PLLA and allylamine (Aldrich). PLLA (1 mmol, 2 g) was dissolved in N,N-dimethylformamide (DMF, Aldrich, HPLC grade) and methylene chloride (MC, Aldrich, HPLC grade) (3:7 v/v %) solvent mixture at room temperature. DCC (1.3 mmol, 0.268 g) and N-hydroxybenzotriazol (HOBT, 1.3 mmol, 0.175 g, Aldrich) were added under nitrogen condition. After 1 h, allylamine (1 mmol, 0.075 g) was added dropwise with moderate stirring and the reaction underwent 5 h at room temperature. After byproduct dicyclohexylurea (DCU) was filtered out, the polymer solution was precipitated in ether (Aldrich) and dried in vacuum for 1 day. The resulting product was washed twice in methanol (Aldrich) to remove remained allylamine, DCC, and HOBT, filtered and dried in vacuum for 1 day.

2.1.2 Synthesis of PNIPAAM Grafted with PLLA.

Poly(N-isopropylacrylamide) (PNIPAAM) grafted with PLLA was synthesized by free radical polymerization. NIPAAM (20 mmol, 2.263 g, Aldrich), PLLA terminated with allyl groups (0.02 mmol, 0.041 g), 2-aminoethanethiol (1 mmol, 0.113 g, Aldrich), and pentanedione peroxide (0.3 mol % of total monomers, Aldrich) as a catalyst were dissolved in DMF (5 ml). The solution was degassed by freezing and sawing method for 3 h in vacuum. The reaction was carried out at 100° C. under nitrogen condition for 4 h. The solution was precipitated with a 10-fold excess of ether, filtered and dried in vacuum for 1 day. To remove any remaining chemical compounds including 2-aminoethanethiol, catalyst, NIPAAM monomers and PLLA terminated with allyl groups, the polymer solution was dialyzed against DMF (MWC-3500, Spectrum laboratories Inc., Rancho Dominguez, Calif.) for 6 h.

2.1.3 Synthesis of Dendrimers.

Fmoc$_8$-Lys$_4$-Lys$_2$-Lys-βAla terminated with carboxylic acid was obtained by cleaving off its linked Wang resin (PLL dendron, Calbiochem-Novabiochem Corp., San Diego, Calif.), in the mixture solvent of trifluoroacetic acid (TFA, Aldrich, 95 vol %), distilled water (2.5 vol %), and triisopropylsilane (TIS, Aldrich, 2.5 vol %) for 2 h, and precipitating in 10-fold excess of cold ether after Wang resin was filtered out using glass filter unit (Chemglass, Vineland, N.J.). The dendrimers were synthesized by DCC coupling reaction of Fmoc$_8$-Lys$_4$-Lys$_2$-Lys-βAla terminated with carboxylic acid and PNIPAAM grafted with PLLA (FIG. 11) in DMF at room temperature for 2 h. The dendrimer solution was precipitated in 10-fold excess of cold ether to remove unreacted reagents and DMF, and further washed four times with cold ether. The product was dried with moderately blowing nitrogen. After drying, the dendrimers were dissolved in piperidine (Aldrich)/DMF (3:7 v:v) to cleave Fmoc (N-alpha-(9-fluorenylmethyloxycarbonyl)) groups. After 15 min, the solutions were precipitated and washed in cold ether five times, dried and stored in freezer.

2.2 Dendrimer Characterization.

2.2.1 Characterization of Dendrimer Chemical Structures.

In order to confirm the success of the dendrimer synthesis, the chemical structures of the PLLA, Allyl-PLLA, PNIPAAM grafted with PLLA, and dendrimer were characterized through studying their infrared absorption bands which match their natural vibrational modes using FTIR (Thermo Nicolet Avetar 370, Madison, Wis.), and through studying their chemical shifts which matched their nuclear spins in a magnetic field using $^1$H NMR (Brukers, DRX-400, Billerica, Mass.). For the FTIR measurements, the polymer solutions were applied on the KBr window (KBr DSC UNIPOL, 20 mm×5 mm, International crystal labs, Garfield, N.J.), and dried at room temperature for 1 day. For the $^1$H-NMR measurements, PLLA, Allyl-PLLA, or PNIPAAM grafted with PLLA was dissolved in CDCl$_3$ (Aldrich), and dendrimer was dissolved in D$_2$O (Alrich), at concentration of 1 mg·ml$^{-1}$. The FTIR spectra of the PLLA and the Allyl-PLLA had no significant difference due to very small amount of allylamine present in the Allyl-PLLA. However, the $^1$H NMR spectrum of the Allyl-PLLA showed new peaks at 6.3 and 5.8 ppm compared to that of the PLLA due to the protons of —CH$_2$=CH— and —CH$_2$=CH—, respectively, and peak at 3.9 ppm due to the protons of —CH$_2$— next to CH$_2$=CH— and peak at 3.5 ppm due to the protons of —CH$_2$— next to —NH—. After the Allyl-PLLA was grafted to the PNIPAAM, the following characteristic FTIR bands were observed, ester C=O stretching of the PLLA at 1764 cm$^{-1}$, —NH— stretching and bending of the PNIPAAM at 3080 cm$^{-1}$ and 1545 cm$^{-1}$, respectively, and amide C=O stretching of the PNIPAAM at 1665 cm$^{-1}$. In addition, the band at 2975 cm$^{-1}$ of the PNIPAAM grafted with PLLA is stronger than the band at 2945 cm$^{-1}$ due to more amount of —CH$_3$ present in the polymer. Moreover, two new characteristic peaks appear in the $^1$H NMR spectrum of the PNIPAAM grafted with PLLA at 4.0 and 1.1 ppm attributed to the protons of —CH—(CH$_3$)$_2$ and —CH—(CH$_3$)$_2$ of the PNIPAAM but not in the $^1$H NMR spectrum of the Allyl-PLLA. After PLL dendrons are attached to the PNIPAAM grafted with PLLA, the FTIR spectrum shows that the band at 2945 cm$^{-1}$ becomes stronger than the band at 2975 cm$^{-1}$ due to great amount of —CH$_2$— present in the PLL dendrons. Moreover, the $^1$H NMR spectrum of the dendrimer shows many more peaks in the region of 1 to 4.5 ppm than the $^1$H NMR spectrum of the PNIPAAM grafted with PLLA due to the protons of —CH$_2$—, >CH— and —NH$_2$— of the branched poly(L-lysine) dendrons.

2.2.2 Characterization of Dendrimer Molar Masses and Molar Mass Distributions.

In order to further confirm the success of the dendrimer synthesis, the molar masses and molar mass distributions of the PNIPAAM, PNIPAAM grafted with PLLA and dendrimer, were determined using matrix assisted laser desoption/ionization time of flight (MALDI-TOF) on Voyager DE-PRO Workstation (Perseptive Biosystems, Framingham, Mass.). For the MALDI-TOF measurements, a $N_2$ laser radiating at 337 nm wavelength with 3 ns pulses was used. The ions generated by the laser pulses were accelerated to 20 kV energy. Dendrimer, PNIPAAM, or PNIPAAM grafted with PLLA, was dissolved in the mixture solvent of $H_2O$ and tetrahydrofuran (THF, Aldrich) at 10 mg·ml$^{-1}$, and then mixed with matrix solvent 2,5-dihydroxybenzoic acid (Aldrich) at 1:9 (v/v, polymer/matrix) ratio. The number and weight average molar masses of the polymers were determined in the linear mode. As shown in Table 3, the molar masses increased with the step of the syntheses, in the order of PLLA (PNIPAAM)<PNIPAAM grafted with PLLA<dendrimer. The dendrimer and the PNIPAAM grafted with PLLA had $M_w$ of 5200 and 3200 g·mol$^{-1}$, respectively, suggesting that two PLL dendrons, whose molar mass is theoretically 1080 g·mol$^{-1}$, was incorporated in both ends of the PNIPAAM grafted with PLLA. The molar mass distribution of the dendrimer is 1.2.

TABLE 3

Molar masses and molar mass distributions of the polymers.

| Sample ID | $M_n$/g · mol$^{-1}$ | $M_w$/g · mol$^{-1}$ | $M_w/M_n$ |
|---|---|---|---|
| PNIPAAM | 1560 | 1732 | 1.1 |
| PNIPAAM grafted with PLLA | 2570 | 3238 | 1.3 |
| Dendrimer | 4270 | 5209 | 1.2 |

2.3 Dendrimer Properties
2.3.1 Thermo-responsive Properties.

Figure 12:
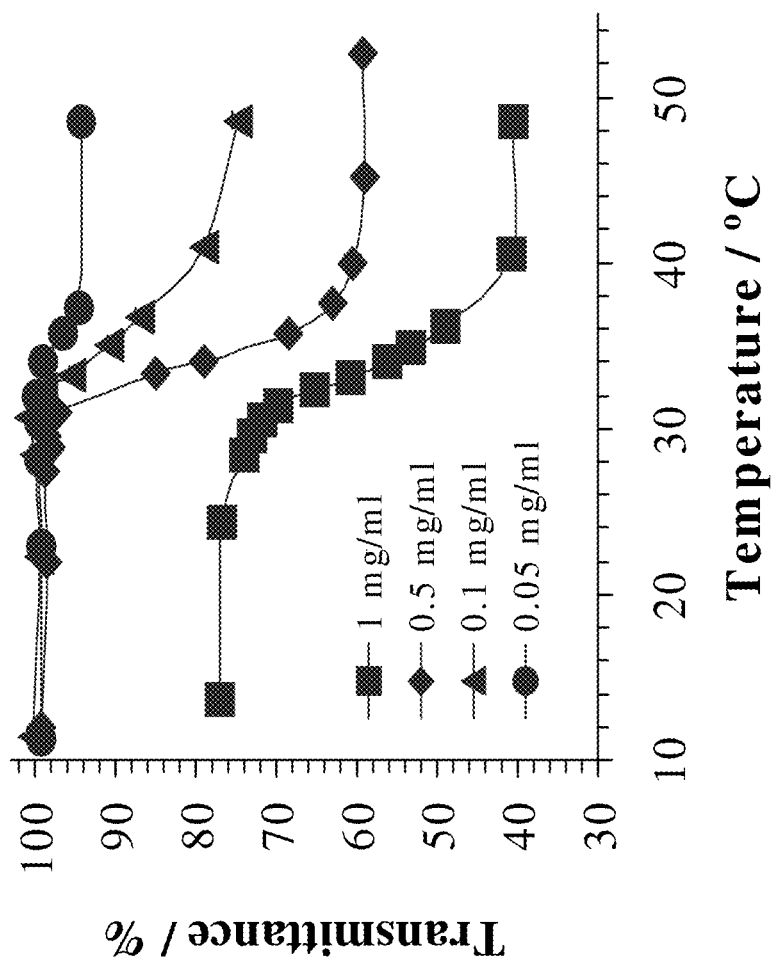
FIG. 12 is a graph showing UV-vis spectra of dendrimers in accordance with one aspect of the present invention in PBS (pH of about 7.4) at 1 (■), 0.5 (♦), 0.1 (▲), and 0.05 (●) mg ml$^{-1}$ as a function of temperature.

UV-vis spectroscopy (Perkin Elmer Lamda 25, Shelton, Conn.) was used to study the transmittances of dendrimers at 500 nm in PBS (pH=7.4) with temperature increase at 1° C./30 min at various concentrations (FIG. 12). The dendrimers were thermo-responsive, showing a lower critical solution temperature (LCST) (defined as temperature at 95% of maximum transmittance) of 31, 32, 34, and 39° C. at concentrations of 1, 0.5, 0.1, and 0.05 mg·ml$^{-1}$, respectively. The LCST became obscure with decreasing concentration of the dendrimers. Above the LCST, the transmittance magnitudes decreased with increasing concentration due to the increase of the interactions of the polymers. The LCST of the PNIPAAM and the PNIPAAM grafted with PLLA decreases linearly with logarithmic concentration, and the latter was 2° C. lower than the former over the concentrations due to the hydrophobicity of the PLLA. However, when PLL is conjugated at both ends of the PNIPAAM grafted with PLLA, the LCST of the dendrimer showed non-linear relationship with logarithmic concentration and the highest value compared to that of other two types of polymers due to the positive charges and hydrophilicity of the PLL.

The thermo-responsive properties of the dendrimers were further confirmed by measuring hydrodynamic sizes of the dendrimers against temperature using dynamic light scattering (DLS) (ALV, Germany). The apparent hydrodynamic diameters $D_h$ of the dendrimers in PBS (pH=7.4) at three concentrations 1, 0.5 and 0.1 mg·ml$^{-1}$ showed a temperature dependence in three regions, respectively (data not shown). In the lower temperature range, $D_h$ decreased slightly as the solution temperature increased, reflecting the contraction of individual chains. In the middle temperature range, $D_h$ increased before reaching their maximum values, showing that the dendrimer nanoparticles aggregated with each other due to interchain association. In the higher temperature range, $D_h$ decreased as the aggregation temperature increased due to intrachain contraction (Lowe et al. 1998a; Siu et al. 2003). The LCST of the dendrimers was 29 (might be between 25 and 29° C.), 30 and 31° C., defined as the initial break points of the $D_h$-temperature curves, at three concentrations 1, 0.5 and 0.1 mg·ml$^{-1}$, respectively. In both the lower and middle temperature ranges, $D_h$ increased with increasing concentrations because interchain interactions also increased with increasing concentrations. The LCST determined by the DLS was slightly lower than that determined by the UV-vis spectroscopy for the same solution concentration, attributed to different instruments for the measurement. Both the DLS and UV-vis results demonstrated that the LCST decreased with increasing concentrations.

2.3.2 Degradation Properties.

Figure 13:
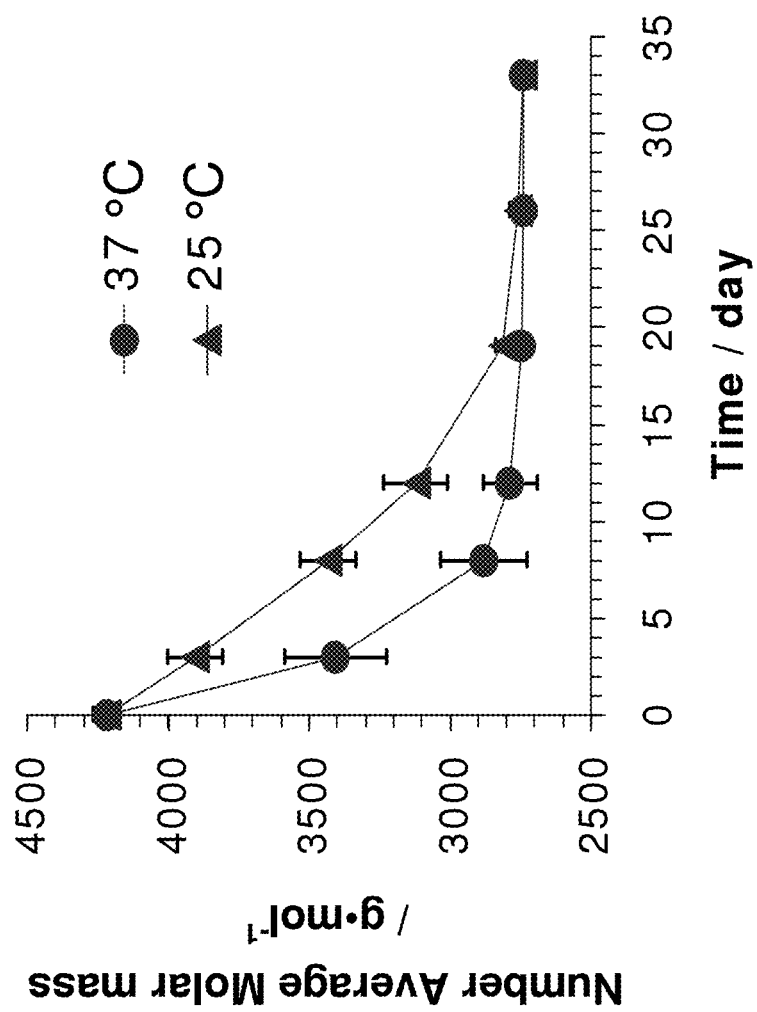
FIG. 13 is a chart illustrating the decomposition of a dendrimer in accordance with one aspect of the present invention by MALDI-TOF analysis of the number average molar mass of the dendrimer at 25 (□) and 37 (■)° C. as a function of time.

Dynamic degradation of dendrimers in PBS (pH=7.4) at 1 mg·ml$^{-1}$ at temperature below and above the LCST, 25 and 37° C., respectively, was probed by measuring molar mass changes of the dendrimers as a function of time using MALDI-TOF (FIG. 13). The number molar mass ($M_n$) of the dendrimers decreased with time for up to one month, and decreased faster at 37° C. than at 25° C., and reach a relatively stable value after 19 days at the both temperatures. Interestingly, the stable $M_n$ after 19 days in FIG. 13 was around 2700 g·mol$^{-1}$, and its subtraction from the initial $M_n$ (around 4200 g·mol$^{-1}$) was around 1500 g·mol$^{-1}$, which was equal to that of the PLLA. The results implied that the dendrimers degraded, and their degradation might be attributed to the hydrolytical degradation of the PLLA component of the dendrimers. To further support the above statement, we measured the FTIR spectra and viscosity of the dendrimers as a function of time, respectively (data not shown). We observed that the peak intensities at ~1760 cm$^1$, which was owned to the ester C=O stretching of PLLA, clearly decreased with time and disappeared after 19 days. Since the peaks at ~1660 cm$^1$, which was attributed to amide C=O stretching of PNIPAAM and PLL, were relatively stable, we used them as reference peaks to normalize the peak intensities at ~1760 cm$^{-1}$. The resulted peak height percentage decreased with time and became 0 after 19 days (data not shown). We also observed that viscosity of the dendrimer (measured by a Cannon-Ubbelohde type viscometer, following the procedures of ASTM D 445 and ISO 3104) decreased with time, decrease faster at 37° C. than at 25° C., and reach a stable value after 19 days (data not shown. Therefore, the FTIR results together with viscometer and MALDI-TOF results, strongly suggested that the designed dendrimers were biodegradable due to the hydrolytic degradation of the PLLA component.

2.4 Dendrimers as Drug Delivery Vehicles
2.4.1 NGF Aqueous Loading and Release.

Mouse nerve growth factor (NGF) in the form of 2.5S (about 24,000 g·mol$^{-1}$, Roche Diagnostics Corp., Indianapolis, Ind.) was loaded the dendrimers in a weight ratio of 1:2 in PBS (pH 7.4, containing 1 w/v % BSA)), sealed and stored at 4° C. for overnight. Free NGF that was not loaded into the dendrimers was removed through three exchanges of the PBS supernatant after ultracentrifugation (Brinkmann Instruments Inc., NY) at 39° C. above the LCST for 1 h. The pellets of the dendrimers loaded with NGF were collected and dried by lyophilization. Approximately 9.1±0.62% loading efficiency was obtained. Loaded NGF did not change the LCST of the dendrimers (data not shown).

For NGF release experiment, dry NGF-loaded dendrimers were dissolved in 1 ml PBS (pH 7.4, containing 1 w/v % BSA) at a concentration of 100 µg·ml$^{-1}$ of the dendrimers at temperature below (25° C.) and above the LCST (37° C.). At selected time points, 5 µl release solution was collected, mixed with 495 µl of PBS (pH 7.4) and centrifuged at 39° C. for 1 h. 100 µl of supernatant was put into 96 well plate and stored at 4° C. for NGF concentration analysis by enzyme-linked immunosorbent assay (ELISA, peo) using a microplate reader (Bio-tek instruments Inc., Winooski, Vt.). 5 µl fresh PBS/BSA (pH 7.4) was added into the release medium to remain its constant volume.

Figure 14:
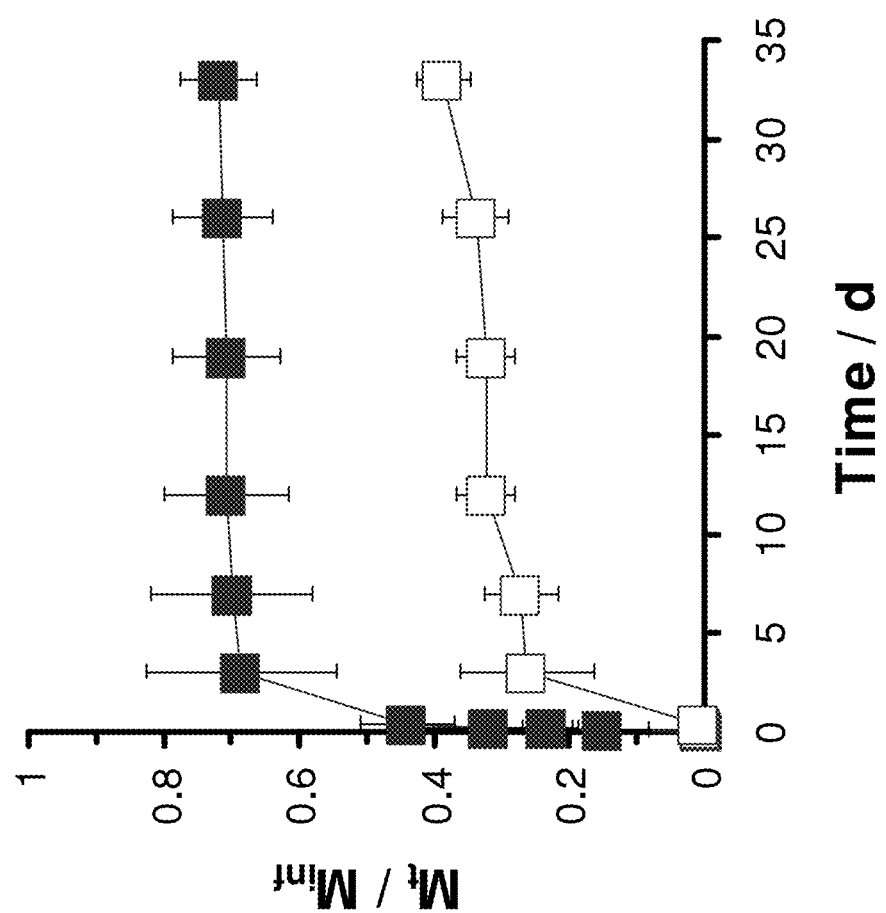
FIG. 14 is a graph showing the NGF release-kinetics from dendrimers in accordance with an embodiment of the present invention at 100 µg ml$^{-1}$ in PBS (pH of about 7.4) at 25 (■) and 37 (□)° C. for 33 days measured by ELISA test (n=5).

The released amount of NGF at 25° C. below the LCST was higher than that at 37° C. above the LCST (FIG. 14). At 25° C., ca. 70% of loaded NGF came out within 3 days because of initial burst effect, and the NGF release amount increased very slowly afterwards. At 37° C., the NGF release profile showed sustained release for up to one month with slight initial burst effects. The reasons might be that the dendrimers were highly swollen below the LCST (25° C.) and the NGF release was controlled mainly by NGF diffusion and the contribution of polymer degradation for the NGF release was low. Above the LCST, the dendrimers were hydrophobic, NGF was relatively harder to diffuse out of the dendrimers and the hydrolytic degradation of the dendrimers played a big role in releasing NGF so that sustained NGF release was achieved.

2.4.2 In Vitro Biological Activities of NGF-Dendrimer Complexes 2.4.2.1 PC12 Cells and Cell Culture.

Rat pheochromocytoma PC12 cells are a clonal cell line derived from rat adrenal chromaffin cells and respond reversibly to NGF stimulation by differentiation into a sympathetic neuron-like phenotype, which develops neurites. Therefore, PC12 cells can be used as a basis assay for evaluating NGF biological activity. In this study, we used PC12 cells to evaluate the biological effects of NGF released from the dendrimers. PC-12 cell (ATCC, Rockville, Md.) were cultured in collagen-coated T-25 cell culture flasks in medium in a humidified incubator at 37° C. and 5% $CO_2$. The cell culture medium (GibcoBRL, Grand Island, N.Y.) consisted of 84% RPMI 1640, 5% fetal bovine serum, 10% heat-inactivated horse serum and 1% penicillin/streptomycin. Cell medium was changed every other day and cells were subcultured once per week. Cells grew attached, and were harvested with trypsin-EDTA (0.05% tripsin with 0.4 mM EDTA).

2.4.2.2 Dendrimer Cell Viability.

Cell viability of the dendrimers was determined using the 3-(4,5-dimethylthiazol-2-yl)-2,5-diphenyltetrazolium bromide (MTT) assay. PC12 cells were plated onto collagen-coated 96-well at a density of 15,000 cells/well (100 µl/well). Plates were incubated at 37° C. for 24 h to allow cell to attach. The polymers, including dendrimers, PNIPAAM alone, and PNIPAAM containing 0.1 mol % PLLA and 0.1 mol % PDLLA, were added in medium at a concentration of 10, 20, 40, 80, 150, and 300 µg ml$^{-1}$. The plates were incubated at 37° C. for 48 h. Then, 10 µl of MTT (5 mg ml$^{-1}$ in RPMI medium) was added to each well. After incubation for 4 h at 37° C., 100 µl of a 50% DMF/20% sodium dodecyl sulfate (pH 4.7) mixture was added. The plates were incubated overnight at 37° C., and then the absorbance at 570 nm was measured using a microplate reader (Bio-tek instruments Inc., Winooski, Vt.) with background subtraction. Cell viability was calculated by dividing the absorbance of wells containing the polymers by absorbance of wells containing medium alone. Average from five replicate wells were used for each sample and control. Cell viability studies revealed that the dendrimer and the polymers consisting core part of the dendrimer, PNIPAAM and PNIPAAM grafted with 0.1 mol % PLLA and 0.1 mol % PDLLA, were not toxic to PC12 cells with above 90% cell viability (99% cell viability for the dendrimer, data not shown) at up to concentration 300 µg·ml$^{-1}$.

2.4.2.3 Biological activities of NGF-dendrimer complexes.

Figure 15:
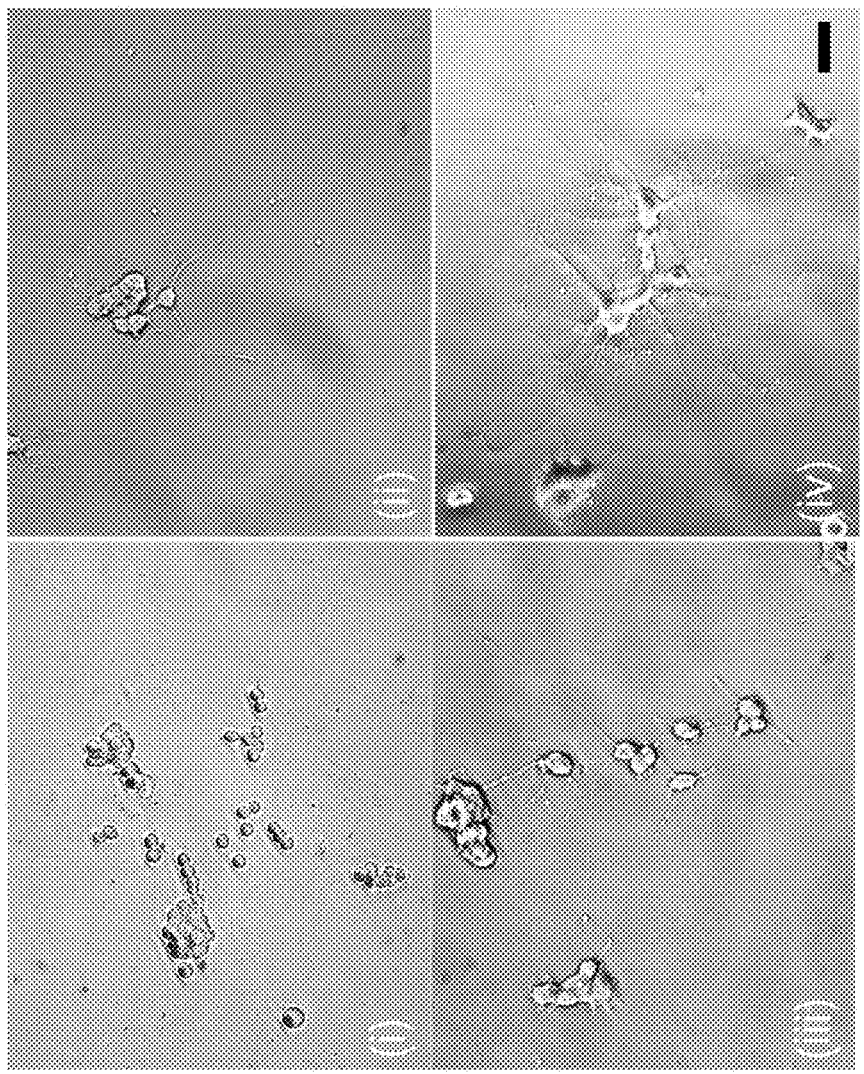
FIG. 15 is an image showing the biological effects of NGF released from dendrimers on a PC12 cell neurite growth, in accordance with an embodiment of the present invention with weight ratio dendrimer:NGF=2:1 at dendrimer concentration 0 (i), 10 (ii), 150 (iii), and 250 (iv) µg ml$^{-1}$ in medium at 37° C. after incubation for 3 days. (-: 50 µm)

Harvested PC12 cells were plated on collagen-coated 48-well plates at a density of 5000 cells/well (200 µl/well). The plates were incubated at 37° C. for 24 h to allow cell to attach. Dendrimers loaded without and with NGF (dendrimer:NGF=2:1, 5:1 and 10:1 weight ratio) were incubated with PC 12 cells at concentrations 50, 100, 150 and 250 µg·ml$^{-1}$ at 37° C. for 1 and 3 days, respectively. Images of neurite outgrowth were observed under an inverted optical microscope (Nikon ECLIPSE TE2000-5), and captured by a digital camera. The number of neurites extending per cell body and the length of neurites greater than the cell body length were counted using a NIH image software. At least 300 PC 12 cells were examined. All the dendrimers loaded with NGF had biological effects on the PC12 cells, by promoting PC12 cell differentiation and neurite outgrowth (FIG. 15). Dendrimer without NGF did not show any effect on neurite outgrowth (data not shown). The results demonstrated that the number of neurites extending per PC12 cell body and the length of neurites greater than the PC12 cell body length, increased with increasing the weight ratios of NGF to dendrimer, the concentrations of the dendrimers and incubation time from 1 to 3 days. The dendrimer loaded with NGF with the weight ratio 2:1 (dendrimer:NGF) and at concentration 250 µg·ml$^{-1}$ had highest neurite length and neurite number per cell body at both day 1 and 3 (data not shown).

2.4.3 In Vitro Dendrimer Permeability Across Biological Barriers 2.4.3.1 Bovine Retinal Microvascular Endothelial Cells (BREC) and Cell Culture.

Retinal vascular endothelia form one aspect of the blood-retinal barrier (BRB) and, like the blood-brain barrier (BBB), control the passage of molecules and cells into the parenchyma. BREC cells were used to test our hypothesis that the dendrimer could penetrate through the BRB and the BBB. BREC cells were seeded at a density of 50,000 cells/cm$^2$ into culture dishes that were precoated with rat-tail collagen and bovine fibronectin. The culture medium consisted of molecular, cellular and developmental biology medium (MCDB-131, Sigma, St Louis, Mo.), 10% fetal bovine serum (FBS), 10 ng·ml$^{-1}$ Epidermal Growth Factor (EGF), 0.2 mg·ml$^{-1}$ ENDO-GRO (VEC Technologies, Inc., Rensselaer, N.Y.), 0.09 mg·ml$^{-1}$ heparin, and antibiotic/antimycotic (penicillin G sodium salt 10 µg·ml$^{-1}$, streptomycin sulfate 25 µg·ml$^{-1}$, and amphotericin B as Fungizone Antimycotic in 0.85% saline, Gibco, Rockville, Md.). The cells were cultured at 37° C. with 95% humidity and 5% $CO_2$. Cells were fed on the third day after seeding and then every other day until confluent monolayers were formed (10-14 days).

2.4.3.2 In Vitro BRB (or BBB) Permeability of Dendrimers Through Thermally Targeting.

BREC cells were grown on a polycarbonate membrane (12-mm diameter; pore size 0.4 µm) filters coated with rat-tail collagen and bovine fibronectin. After confluent monolayers were formed, the membranes were used for permeability studies as an open two-compartments vertical side-by-side dynamic model. The basolateral and the apical chambers contained 1.5 and 0.5 ml of culture medium, respectively, to ensure no change in pressure gradient existed. The Dendrimer labeled with fluorescein-5'-isothiocyanate (FITC, Sigma-Aldrich, Milwaukee, Wis.) was dissolved in media and added to the apical chamber of each well at a concentration of 100 and 200 µg·ml$^{-1}$. Transport experiments were conducted in the apical to basal direction at 37° C. for every one hour up to 5 hours. 100 µl samples were taken from the basolateral chamber and the volume was replaced with fresh culture medium. Fluorescence of aliquots was quantified on a FluorImager 595 (Molecular Dynamics).

The dendrimer at both concentrations of 100 and 200 µg·ml$^{-1}$ penetrated through the BRB nearly linearly with increasing time. The percentage of the dendrimer penetrating through the BRB increased with increasing concentration from 100 to 200 µg·ml$^{-1}$ (data not shown). As shown before, the dendrimer had a LCST of 34° C. at 100 µg·ml$^{-1}$ and the LCST decreased with increasing concentration. Therefore, the LCSTs of the dendrimer at 100 and 200 µg·ml$^{-1}$ were both lower than 37° C., and the dendrimer was hydrophobic at 37° C. The reasons for the penetration of the dendrimer through the BRB might be because of electrostatic interaction of the polyamine groups of the dendrimer with the negatively charged groups of the BREC cells through absorptive-mediated endocytosis mechanism (Tamai et al. 1996; Hong et al. 2000; Bickel et al. 2001); and hydrophobic interaction of the dendrimer and the BREC cells through receptor-mediated endocytosis mechanism (Tamai et al. 1996; Bickel et al. 2001; Qian et al. 2002).

2.4.4 Thermally uptake of Dendrimers by Neuron Cells.

FITC-labeled dendrimer was added into one day cultured PC 12 cells at a concentration of 100 µg·ml$^{-1}$ of the dendrimers and incubated at temperature below (25° C.) and above the LCST (37° C.) for 1 h. The cells were harvested, resuspended in PBS (pH 7.4), and fixed with 4% paraformaldehyde for 20 min after trypan blue, an extracellular fluorescence-quenching dye, was added at a concentration of 0.5% (w/v) for 5 min to wash membrane-bound dendrimers. The quantitative PC12 cellular uptake of FITC-labeled dendrimers was measured by flow cytometry at 530 nm using a fluorescence-activated cell scanner (Becton Dickinson, San Jose, Calif.) equipped with an argon-ion laser.

The amount of internalized dendrimer into PC12 neuron cells was quantitatively calculated by flow cytometry. An about 70% and 90% of PC12 neuron cells were associated with FITC-labeled dendrimer at 25 and 37° C., respectively (not shown). To remove thermo-responsive dendrimer with FITC attached to cell exterior, we used a trypan blue quenching dye to confirm that detected dendrimer was internalized and not stayed in the cell surface. The fluorescence of dendrimer decreased 35% (25° C.) and 5% (37° C.) (not shown) after trypan blue quenching, confirming that 50% (25° C.) and 95% (37° C.) of dendrimer associated with PC12 neuron cells was internalized. The results suggested that the alterations of dendrimer's properties in response to temperature can be used for targeted drug delivery through thermally targeting strategy.

Only the preferred embodiment of the present invention and examples of its versatility are shown and described in the present disclosure. It is to be understood that the present invention is capable of use in various other combinations and environments and is capable of changes or modifications within the scope of the inventive concept as expressed herein. Thus, for example, those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A dendrimer comprising a poly(N-isopropylacrylamide) segment or derivative thereof, a poly(lysine) segment or derivative thereof, and a poly(lactic acid) segment or derivative thereof, wherein the derivative of the poly(N-isopropylacrylamide) segment is selected from the group consisting of: a poly(N-isopropylmethacrylamide), and a poly(N-n-propylacrylamide), wherein the derivative of the poly(lysine) segment is a poly(L-lysine); and wherein the derivative of the poly(lactic acid) segment is selected from the group consisting of: a poly(ethylene oxide)-co-poly(L-lactic acid), a poly (L-lactic acid), a poly(D,L-lactic acid), a poly(lactide-co-glycolides) (PLGA), and a biotinylated poly(ethylene glycol-block-lactic acid).

2. The dendrimer of claim 1, wherein the poly(N-isopropylacrylamide) segment or derivative thereof has a number average molar mass of between about 1000 and about 600,000 g·mol$^{-1}$, the poly(lysine) segment or derivative thereof has a number average molar mass of between about 150 and about 600,000 g·mol$^{-1}$, and the poly(lactic acid) segment or derivative thereof has a number average molecular weight of between about 100 and about 600,000 g·mol$^{-1}$.

3. The dendrimer of claim 2, wherein the poly(lysine) segment or derivative thereof is a poly(L-lysine) or derivative thereof and the poly(lactic acid) segment or derivative thereof is a poly(D,L-lactic acid) segment or a derivative thereof.

4. A pharmaceutical composition comprising the polymeric material of claim 1 and a substance.

5. The pharmaceutical composition of claim 4, wherein the substance is a biologically active substance.

6. The pharmaceutical composition of claim 4, wherein the biologically active substance comprises a protein, peptide, gene, enzyme, antibody, antibiotic, nucleic acid, DNA, RNA, receptor, hormone, vaccine or drug.

7. The pharmaceutical composition of claim 5, wherein the biologically active substance comprises interferon consensus, interleukin, erythropoietin, granulocyte-colony stimulating factor (GCSF), stem cell factor (SCI:), leptin (OB protein), interferon (alpha, beta, gamma), ciprofloxacin, amoxycillin, lactobacillus, cefotaxime, levofloxacin, cefipime, mebendazole, ampicillin, lactobacillus, cloxacillin, norfloxacin, tinidazole, cefpodoxime, proxctil, azithromycin, gatifloxacin, roxithromycin, cephalosporin, anti-thrombogenics, aspirin, ticlopidine, sulfinpyrazone, heparin, warfarin, growth factors, differentiation factors, hepatocyte stimulating factor, plasmacytoma growth factor, brain derived neurotrophic factor (BDNF), glial derived neurotrophic factor (GDNF), neurotrophic factor 3 (NT3), fibroblast growth factor (FGF), transforming growth factor(TGF), platelet transforming growth factor, milk growth factor, endothelial growth factors (EGF), endothelial cell-derived growth factors (ECDGF), alpha-endothelial growth factors, beta-endothelial growth factor, neurotrophic growth factor , nerve growth factor (NGF), vascular endothelial growth factor (VEGF), 4-1 BB receptor (4-1BBR), TRAIL (TNF-related apoptosis inducing ligand), artemin (GFRalpha3-RET ligand), BCA-1 (B cell-attracting chemokine 1), B lymphocyte chemoattractant (BLC), B cell maturation protein (BCMA), brain-derived neurotrophic factor (BDNF), bone growth factor such as osteoprotegerin (OPG), bone-derived growth factor, megakaryocyte derived growth factor (MGDF), keratinocyte growth factor (KGF), thrombopoietin, platelet-derived growth factor (PGDF), megakaryocyte derived growth factor (MGDF), keratinocyte growth factor (KGF), platelet-derived growth factor (PGDF), bone morphogenetic protein 2 (BMP2), BRAK, C-10, Cardiotrophin 1 (CTI), CCR8, anti-inflammatory: paracetamol, salsalate, diflunisal, mefenamic acid, diclofenac, piroxicam, ketoprofen, dipyrone, acetylsalicylic acid, antimicrobials amoxicillin, ampicillin, cephalosporins, erythromycin, tetracyclines, penicillins, trimethprim-sulfamethoxazole, quniolones, amoxicillin, clavulanatf,azithromycin, clarithromycin, anticancer drugs aliteretinoin, altertamine, anastrozole, azathioprine, bicalutamide, busulfan, capecitabine, carboplatin, cisplatin, cyclophosphamide, cytarabine, doxorubicin, epirubicin, etoposide, exemestane, vincristine, vinorelbine, hormones, thyroid stimulating hormone (TSH), sex hormone binding globulin (SHBG), prolactin, luteotropic hormone (LTH), lactogenic hormone, parathyroid hormone (PTH), melanin concentrating hormone (MCH), luteinizing hormone (LHb), growth hormone (HGH), follicle stimulating hormone (FSHb), haloperidol, indomethacin, doxorubicin, epirubicin, amphotericin B, Taxol, cyclophosphamide, cisplatin, methotrexate, pyrene, amphotericin B, anti-dyskinesia agents, Alzheimer vaccine, antiparkinson agents, ions, edetic acid, nutrients, glucocorticoids, heparin, anticoagulation agents, anti-virus agents, anti-HIV agents, polyamine, histamine cystineamine diphenhydramine orphenadrine muscarinic antagonist, phenoxybenzamine and derivatives thereof, protein A, streptavidin, amino acid, beta-galactosidase, methylene blue, protein kinases, beta-amyloid, lipopolysaccharides, eukaryotic initiation factor-4G, tumor necrosis factor (TNF), tumor necrosis factor-binding protein (TNF-bp), interleukin-1 (to 18) receptor antagonist (IL- Ira), granulocyte macrophage colony stimulating factor (GM-CSF), novel erythropoiesis stimulating protein (NESP), thrombopoietin, tissue plasminogen activator (TPA), urokinase, streptokinase, kallikrein, insulin, steroid, acetylsalicylic acid, acetaminophen, analgesic, anti-tumor preparation, anti-cancer preparation, anti-proliferative preparation or pro-apoptotic preparation.

8. A method of administering a composition to a subject in need thereof, the method comprising administering the pharmaceutical composition of claim 4 to the subject.

9. The method of claim 8, wherein the subject is human.

10. The method of claim 9, wherein the composition comprises a biologically active substance and the composition is administered wherein the biologically active substance has a concentration of up to approximately 1000 mg·ml$^{-1}$.

11. A method of aqueously loading a biologically active substance, the method comprising combining the dendrimer of claim 1 with a biologically active substance in an aqueous medium to form a composition comprising the dendrimer and the biologically active substance.

12. The method of claim 11, comprising forming the composition wherein the biologically active substance comprises approximately 40 wt % of the composition.

13. A dendrimer comprising a smart segment, a biodegradable segment, and a poly(lysine) segment,
wherein the smart segment comprises a poly(N-isopropylacrylamide), a poly(N-isopropylacrylamide) derivative comprises a poly(N-alkylacrylamide), a poly(N-n-propylacrylamide), a poly(N-isopropylmethacrylamide), or a substance that is derived from any of these smart segment molecules with similar structure and properties;
wherein the hydrophobic segment comprises a polyester, a polylactide, a poly(L-lactic acid), a poly(D,L-lactic acid), a poly(lactide-co-glycolides), a biotinylated poly (ethylene glycol-block-lactic acid), a poly(alkylcyanoacrylate), a poly(epsilon-caprolactone), a polyanhydride, a poly(bis(p-carboxyphenoxy) propane-sebacic acid), a polyorthoester, a polyphosphoester, a polyphosphazene, a polyurethane, a poly(amino acid), or a substance that is derived from any of these hydrophobic segments with similar structure and properties; and,
wherein the poly(lysine) segment comprises poly(lysine) or a substance that is derived from poly(lysine) with similar structure and properties.

14. The dendrimer of claim 13, wherein the smart segment has a number average molar mass of between about 1000 and about 600,000 g·mol$^{-1}$, the biodegradable segment has a number average molecular weight of between about 100 and about 600,000 g·mol$^{-1}$, and the poly(lysine) segment has a number average molar mass of between about 150 and about 600,000 g·mol$^{-1}$.

* * * * *